US005676923A

United States Patent [19]

Platzek et al.

[11] Patent Number: 5,676,923
[45] Date of Patent: Oct. 14, 1997

[54] SUBSTITUTED DTPA MONOAMIDES OF THE CENTRAL CARBOXYLIC ACID GROUP AND THEIR METAL COMPLEXES

[75] Inventors: Johannes Platzek; Ulrich Niedballa; Peter Mareski; Bernd Raduchel; Hanns-Joachim Weinmann, all of Berlin; Andreas Muhler, Neuenhagen; Bernd Misselwitz, Berlin, all of Germany

[73] Assignee: Schering Aktiengesellschaft, Berlin, Germany

[21] Appl. No.: 484,319

[22] Filed: Jun. 7, 1995

[30] Foreign Application Priority Data

Feb. 21, 1995 [DE] Germany ............... 195 07 822.5

[51] Int. Cl.⁶ ............... C07D 225/02; C07D 211/70; A61K 49/04; C07C 321/00; C07C 271/02; C07C 229/02; C07F 9/94; C07F 13/00; C07F 1/08; C07F 1/10; C07F 1/12

[52] U.S. Cl. ............... 424/4; 424/5; 540/450; 540/484; 544/106; 546/348; 548/416; 548/517; 548/530; 548/540; 548/336.1; 548/491; 548/400; 560/9; 560/10; 560/18; 560/24; 560/28; 560/29; 560/37; 560/38; 560/39; 560/40; 560/147; 560/148; 560/157; 560/160; 534/13; 534/14; 534/16; 514/494; 514/497; 514/499; 514/501; 514/502; 514/503; 514/504; 514/836; 562/431; 562/443; 562/444; 562/445; 562/450; 562/556; 562/561; 562/566; 556/44; 556/49; 556/50; 556/55; 556/56; 556/62; 556/63; 556/107; 556/116; 556/117; 556/134; 556/136; 556/148

[58] Field of Search ............... 540/450, 484; 546/348; 548/416, 517, 530, 540, 336.1, 491, 400; 560/9, 10, 18, 24, 28, 37, 38, 39, 40, 29, 147, 148, 157, 160; 562/431, 443, 444, 445, 450, 556, 561, 566, 448; 556/44, 49, 50, 55, 56, 62, 63, 107, 116, 117, 134, 136, 148; 534/13, 14, 16; 514/495, 497, 499, 501, 502, 503, 505, 836; 544/106; 424/4, 5

[56] References Cited

U.S. PATENT DOCUMENTS

| | | |
|---|---|---|
| 4,647,447 | 3/1987 | Gries et al. |
| 4,925,804 | 5/1990 | Hale et al. |
| 4,957,939 | 9/1990 | Gries et al. |
| 4,963,344 | 10/1990 | Gries et al. |
| 5,017,533 | 5/1991 | Newkirk et al. |
| 5,077,037 | 12/1991 | Wallace ............... 424/9 |
| 5,137,711 | 8/1992 | Weber et al. ............... 424/9 |
| 5,362,475 | 11/1994 | Gries et al. |
| 5,399,340 | 3/1995 | Radüchel et al. |

FOREIGN PATENT DOCUMENTS

| | | |
|---|---|---|
| 353350 | 7/1988 | European Pat. Off. |
| 450742 | 10/1991 | European Pat. Off. |
| 36 21 026 | 12/1987 | Germany |

*Primary Examiner*—Joseph Conrad
*Attorney, Agent, or Firm*—Millen, White, Zelane & Branigan, P.C.

[57] ABSTRACT

Diethylenetriaminepentaacetic acid monoamide derivatives, their complexes and complex salts, containing an element of atomic numbers 21-29, 31, 32, 39, 42-44, 49 or 57-83, pharmaceutical agents containing these compounds, their use as contrast media and process for their production.

15 Claims, No Drawings

SUBSTITUTED DTPA MONOAMIDES OF THE CENTRAL CARBOXYLIC ACID GROUP AND THEIR METAL COMPLEXES

The invention relates to diethylenetriaminepentaacetic acid monoamide derivatives, their complexes and complex salts, pharmaceutical agents containing these compounds, their use as NMR contrast media and process for their production.

BACKGROUND OF THE INVENTION

At the beginning of the 1950s, metal complexes were already considered as contrast media for radiology. But the compounds used at that time proved difficult to tolerate, so that a use in humans was not suitable. It was therefore very surprising that certain complex salts proved sufficiently compatible so that a routine use in humans could be taken into consideration.

In EP 71564 B1, i.a., the meglumine salt of the gadolinium(III) complex of diethylenetriaminepentaacetic acid (DTPA) is described as a contrast medium for NMR tomography. A preparation which contains this complex was approved worldwide under the name Magnevist® as the first NMR contrast medium. After intravenous administration, this contrast medium spreads extracellularly and is excreted renally by glomerular secretion. A passage of intact cell membranes is practically not observed. Magnevist® is especially well-suited for the visualization of pathological areas (e.g., inflammations, tumors).

But for the visualization of non-inflammatory and non-tumorous tissue parts, there is still a need for new contrast media, which exhibit a higher organ specificity or are excreted extrarenally.

For use as NMR contrast media, a number of DTPA derivatives with terminal amide linkages were proposed in patent specifications EP 0263051 A1, EP 0450742 A1 and EP 0413405 A1. But these compounds have not completely met the expectations, connected with their production, with respect to compatibility and pharmacokinetics.

In addition, in their clinical use, all previously known complexes and their salts cause problems with respect to compatibility and/or stability. The diagnostically valuable use of heavy elements as components of x-ray contrast media to be administered parenterally previously came to nothing due to the insufficient compatibility of such compounds. The difference between the effective dose and the dose that is toxic in animal experiments is relatively small in the case of paramagnetic substances previously proposed or tested for nuclear spin tomography. They further exhibit an excessively small organ specificity. Moreover, their contrast-enhancing effect and their compatibility are insufficient in many cases.

Further, for many purposes, there is therefore a need particularly for more compatible, but also stable, readily soluble and sufficiently organ-specific complex compounds.

SUMMARY OF THE INVENTION

An object of the invention is thus to make available these compounds and agents as well as to provide a process for their production. This object is achieved by the invention as described herein. Upon further study of the specification and appended claims, further objects and advantages of this invention will become apparent to those skilled in the art.

It has been found that compounds which consist of the anion of a complexing derivatized monoamide of the central carboxylic acid group of diethylenetriaminepentaacetic acid and one or more central ions of an element of atomic numbers 21–29, 31, 32, 39, 42–44, 49 or 57–83 and optionally one or more cations of an organic and/or inorganic base or amino acid are surprisingly excellently suited for the production of NMR, x-ray and radiodiagnostic agents as well as radiotherapeutic agents.

The compounds according to the invention are described by general formula I

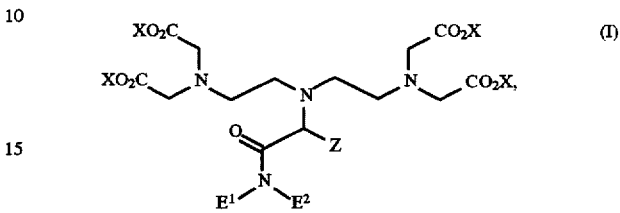

in which

X independently of one another, each stand for a hydrogen atom or a metal ion equivalent of an element of atomic numbers 20–29, 31, 32, 39, 42–44, 49 or 57–83, Z, $E^1$, $E^2$ independently of one another, each stand for a saturated or unsaturated, branched or straight-chain $C_1$–$C_{50}$ alkyl chain, wherein:

the chain or parts of this chain optionally form a cyclic $C_5$–$C_8$ unit or a bicyclic $C_{10}$–$C_{14}$ unit, the alkyl chain may also contain, i.e., be interrupted by, 0 to 10 oxygen atoms and/or 0 to 2 sulfur atoms and/or 0 to 3 carbonyl groups, 0 to 1 thiocarbonyl groups, 0 to 2 imino groups, 0 to 2 phenylene groups, 0 to 1 3-indole groups, 0 to 1 methyl-imidazol-4-yl groups and/or 0 to 3 N-$R^3$ groups, and the alkyl chain may be substituted by 0 to 2 phenyl, 0 to 2 pyridyl, 0 to 5 $R_2O$, 0 to 1 HS, 0 to 4 $R^2OOC$, 0 to 4 $R^2OOC$—$C_{1-4}$ alkyl and/or 0 to 1 $R^2(H)N$ groups, in which optionally present aromatic groups can be substituted zero to five times, independently of one another, by fluorine, $R^2O_2C$, $R^2OOC$—$C_{1-4}$ alkyl, $R^2NHOC$, $R^2CONH$, $O_2N$, $R_2O$, and/or $R^2$ groups, $R^2$ independently of one another, each stand for a hydrogen atom or a straight-chain or branched $C_1$–$C_4$ alkyl radical and $R^3$ independently of one another, each stand for a hydrogen atom or a straight-chain or branched, saturated or unsaturated $C_1$–$C_{30}$ alkyl radical and $E^1$, $E^2$ in addition to the above-indicated meaning, can stand for a hydrogen atom or $E^1$ and $E^2$ together with inclusion of the nitrogen atom, stand for a five- to eight-membered, saturated or unsaturated heterocycle, which optionally contains in the ring one to two additional nitrogen, oxygen or sulfur atoms and/or carbonyl groups, in which the HO and/or $H_2N$ and/or HS and/or HOOC group(s) optionally contained in Z, $E^1$ and/or $E^2$ can be present in protected form, as described below, and in which free carboxylic acid groups not used for complexing can also be present as salts with physiologically compatible inorganic and/or organic cations or as esters or amides. The invention therefore relates to the compounds of general formula I, and complexes thereof.

Compounds of general formula I with all X groups meaning hydrogen are referred to below as complexing agents; compounds of general formula I, in which at least two radicals X have the meaning of a metal ion equivalent, are referred to as complexes. Salts of the complexes of general formula I, in which organic and/or inorganic bases act as counterion(s), are referred to below as complex salts.

The designations of terminal or central carboxylic acids in DTPA can be defined as follows:

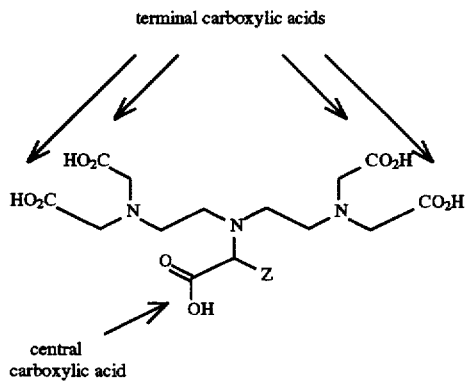

As preferred groups $E^1$ or $E^2$, there can be mentioned as examples the hydrogen atom, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, cyclopentyl, cyclohexyl, cycloheptyl, cyclooctyl, cyclohexenyl, cyclopentanone, cyclohexanol, cyclohexenol, 2-aminocycloheptane, 2-hydroxyethyl, 5-oxononyl, hex-5-enyl, icosa-19-enyl, 2-ethylhexyl, 2-ethoxyhexyl, phenyl, benzyl, naphthyl, imidazolyl, thiazolyl radicals, as well as radicals of formulae:

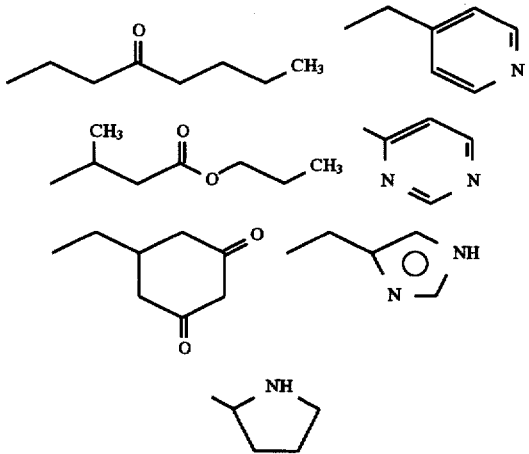

Preferred groups $E^1$ and $E^2$ are straight-chain alkyl radicals with up to 20 carbon atoms, hydrogen atoms, cyclohexyl, phenyl, benzyl, naphthyl radicals as well as radicals of general formula IV

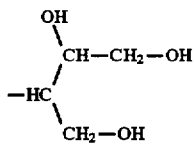

(IV)

as well as radicals of composition

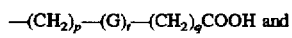

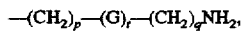

in which
G stands for oxygen or sulfur, p,q independently of one another, each stand for a number of from 1 to 28,
t stands for 0 or 1, and
p+t+q≦30, where the acid group can also be present as a salt of an inorganic or organic base, as an ester or as an amide, or the amino group can also be present as ammonium salt with a physiologically compatible anion or as an amide.

As groups in which $E^1$ and $E^2$, together with inclusion of the nitrogen atom, form a five- to eight-membered, saturated or unsaturated heterocycle, there can be mentioned as examples the imidazolyl, pyrazolyl, pyrrolyl, 3-pyrrolinyl, pyrrolidinyl, morpholinyl group or the piperidinyl group.

As radicals Z, there can be mentioned as examples methyl, ethyl, n-propyl, i-propyl, n-butyl, i-butyl, pentyl, hexyl, cyclohexyl radicals or phenyl or benzyl radicals, as well as radicals of formulae:

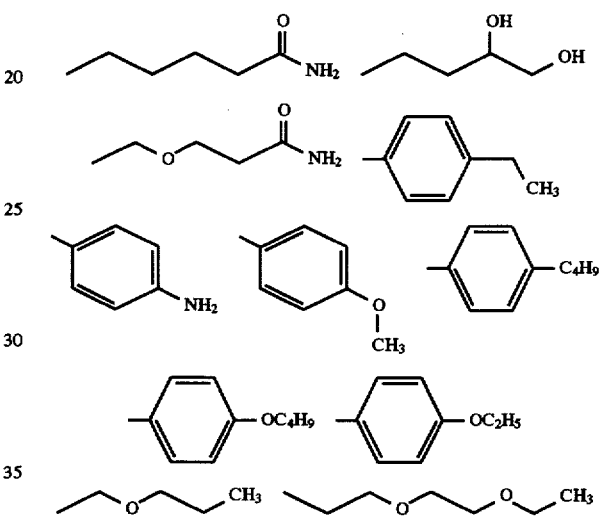

Radical Z can also contain, for example, a 3-indole radical and/or a histidine radical.

Preferred radicals Z are alkyl and cycloalkyl radicals, such as the methyl, ethyl, propyl, i-propyl, butyl, i-butyl, tert-butyl, pentyl, hexyl or cyclohexyl radical, as well as the phenyl and the benzyl radical.

Preferred radicals Z are especially groups which are identical with radicals $Z^A$ occurring in naturally occurring amino acids of general formula III.

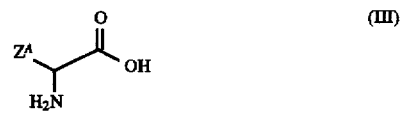

(III)

These $Z^A$ groups are:

| | |
|---|---|
| —CH₃ | Ala |
| —CH(CH₃)₂ | Val |
| —CH₂—CH(CH₃)₂ | Leu |
| —CH₂—Ph | Phl |
| —CH₂—⌬—OH | Tyr |
| —CH₂OH | Ser |
| —CH(OH)—CH₃ | Thr |
| —CH₂SH | Cys |

-continued

| | |
|---|---|
| —CH$_2$—SCH$_3$ | Met |
| 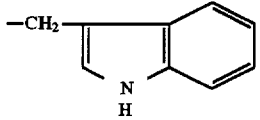 —CH$_2$— (indole) | Try |
| —CH$_2$CO$_2$H | Asp |
| —CH$_2$CH$_2$—CO$_2$H | Glu |
| 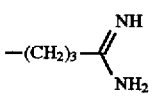 —(CH$_2$)$_3$—NH—C(=NH)NH$_2$ | Arg |
| —(CH$_2$)$_4$—NH$_2$ | Lys |
| 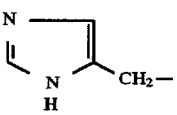 (imidazolyl-CH$_2$—) | His |

The —OH and/or —NH$_2$ and/or —SH and/or —COOH group(s) optionally contained in Z and/or $E^1$ and/or $E^2$ can be present in this case in protected form. Details of syntheses with protective groups are further summarized below.

Production of the Complexes and Complexing Agents According to the Invention

The invention also relates to a process for the production of complexes and complexing agents according to the invention.

The production of the complexes according to the invention takes place in the way analogous to that disclosed in patent specifications EP 71564, EP 130934 and DE-OS 3401052, by the metal oxide or a metal salt (for example, a chloride, nitrate, acetate, carbonate or sulfate) of the element of atomic numbers 21–29, 31, 32, 39, 42–44, 49 or 57–83 being dissolved or suspended in water and/or a lower alcohol (such as methanol, ethanol or isopropanol) and being reacted with the solution or suspension of the equivalent amount of the complexing agent of general formula I according to the invention and then, if desired, existing acid hydrogen atoms of the acid groups being substituted by cations of inorganic and/or organic bases or amino acids.

In this case, the neutralization takes place with the help of inorganic bases (e.g., hydroxides, carbonates or bicarbonates) of, e.g., sodium, potassium or lithium and/or organic bases, such as, i.a., primary, secondary and tertiary amines, such as, e.g., ethanolamine, glucamine, N-methyl and N,N-dimethyl-glucamine, as well as basic amino acids, such as, e.g., lysine, arginine and ornithine.

For the production of neutral complex compounds, enough of the desired bases can be added, for example, to the acid complex salts in aqueous solution or suspension so that the neutral point is reached. The resulting solution can then be evaporated to dryness in a vacuum. It is often advantageous to precipitate the neutral salts that are formed by adding water-miscible solvents, such as, e.g., lower alcohols (methanol, ethanol, isopropanol, etc.), lower ketones (acetone, etc.), polar ethers (tetrahydrofuran, dioxane, 1,2-dimethoxyethane, etc.) and thus to obtain easily isolated and readily purified crystallizates. It has proven especially advantageous to add the desired base as early as possible during the complexing of the reaction mixture and thus to save a process step.

If the acid complexes contain several free acid groups, it is often suitable to produce neutral mixed salts, which contain both inorganic and organic cations as counterions.

This can happen, for example, by the complexing agents being reacted in aqueous suspension or solution with the oxide or salt of the desired element and half of the amount of an organic base required for neutralization, the formed complex salt being isolated, optionally purified and then mixed with the required amount of inorganic base for complete neutralization. The sequence of the addition of base can also be reversed.

Another possibility to arrive at neutral complex compounds consists in converting the remaining acid groups, as described, e.g., in EP 0450742, completely or partially to esters or amides.

If the agents according to the invention are to contain radioisotopes, the production of the complexes from the complexing agents can take place according to the methods described in "Radiotracers for Medical Applications," Vol. I, CRC Press, Boca Raton, Fla.

The production of the complexing agents of general formula I according to the invention takes place by cleavage of acid protective groups $R^1$ from compounds of general formula IV

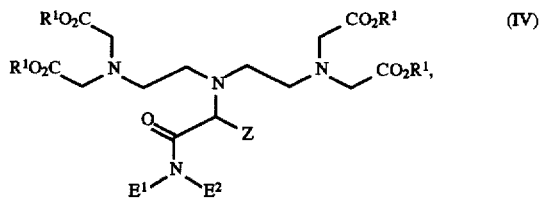

(IV)

in which $R^1$ stands for an acid protective group, and Z, $E^1$ and $E^2$ have the above-indicated meaning. As examples for acid protective groups $R^1$, straight-chain and branched $C_1$–$C_4$ alkyl and benzyl groups can be mentioned. The tert-butyl group and the benzyl group are preferably used.

The cleavage of the protective groups takes place according to the processes known to one skilled in the art, for example, by hydrolysis, hydrogenolysis, alkaline saponification of esters with alkali in aqueous-alcoholic solution at temperatures of 0° to 50° C., acid saponification with mineral acids or, in the case of tert-butyl esters, with the help of trifluoroacetic acid. Preferred are the hydrogenolytic cleavage of the benzyl group and the saponification of the tert-butyl group with trifluoroacetic acid.

The production of the compounds of general formula IV takes place in that compounds of general formula V

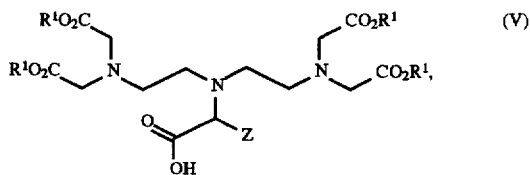

(V)

in which Z and $R^1$ have the above-mentioned meaning, after activation of the free carboxylic acid group, are reacted with amines of general formula VI

(VI)

in the way known to one skilled in the art.

The linkage of compounds of general formula V with the amines of general formula VI takes place in organic solvents such as toluene or tetrahydrofuran at temperatures of −10° C. to 50° C., preferably at room temperature and below, with addition of one or more activating reagents.

The activation can take place, for example, by reaction of acid with dicyclohexylcarbodiimide, N-hydroxysuccinimide/dicyclohexylcarbodiimide, carbonyldiimidazole, 2-ethoxy-1-ethoxycarbonyl-1,2-dihydroquinoline, oxalic acid dichloride or isobutyl chloroformate in the way described in the literature, for example:

- Aktivierung von Carbonsäuren [Activation of Carboxylic Acids]. Übersicht in Houben-Weyl, Methoden der Organischen Chemie [Survey in Houben-Weyl, Methods of Organic Chemistry], Volume XV/2, Georg Thieme Verlag Stuttgart, 19.
- Aktivierung mit Carbodiimiden [Activation with Carbodiimides]. R. Schwyzer and H. Kappeler, Helv. 46: 1550 (1963).
- E. Wünsch et al., B. 100:173 (1967).
- Aktivierung mit Carbodiimiden/Hydroxysuccinimid [Activation with Carbodiimides/Hydroxysuccinimide]: J. Am. Chem. Soc. 86: 1839 (1964) as well as J. Org. Chem. 53: 3583 (1988). Synthesis 453 (1972).
- Anhydridmethode, 2-Ethoxy-1-ethoxycarbonyl-1,2-dihydrochinolin [Anhydride Methods, 2-Ethoxy-1-ethoxycarbonyl-1,2-dihydroquinoline]: B. Belleau et al., J. Am. Chem. Soc., 90: 1651 (1986), H. Kunz et al., Int. J. Pept. Prot. Res., 26: 493 (1985) and J. R. Voughn, Am. Soc. 73: 3547 (1951).
- Imidazolid-Methode [Imidazolide Methods]: B. F. Gisin, R. B. Menifield, D. C. Tosteon, Am. Soc. 91: 2691 (1969).
- Säurechlorid-Methoden, Thionylchlorid [Acid Chloride Methods, Thionyl Chloride]: Helv., 42: 1653 (1959).
- Oxalylchlorid [Oxalyl Chloride]: J. Org. Chem., 29: 843 (1964).

Numerous amines, which correspond to general formula VI

in which $E^1$ and $E^2$ have the above-mentioned meanings, can be purchased (e.g.: E. Merck, Darmstadt, Fluka Chemie AG, CH-9470 Buchs) or can be produced as described, e.g., in Houben-Weyl, Methoden der organischen Chemie, Stickstoffverbindungen II [Nitrogen Compounds II], Volumes XI/1 and XI/2, Georg Thieme Verlag Stuttgart, 1957.

As amines of general formula VI, there can be mentioned as examples ammonia, methylamine, dimethylamine, ethylamine, diethylamine, isopropylamine, diisopropylamine, cyclohexylamine, dicyclohexylamine, diisopropenylamine, cyclohexenylamine, 2-hydroxyethylamine, 5-oxononylamine, hex-5-enylamine, 2-ethylhexylamine, 2-ethoxyhexylamine, aniline, benzylamine, naphthylamine, piperidine, N-ethylpiperazine, 4-hydroxymethylpiperidine, 4-(2-hydroxyethyl)-piperidine, 4-piperidone, piperidine-3-carboxylic acid diethylamide, piperidine-4-carboxylic acid dimethylamide, 2,6-dimethylpiperidine, N-acetylpiperazine, pyrazoline, oxazolidine, imidazole or thiazole. The preferred radicals for $E^1$ and $E^2$ were already mentioned above.

The HO, HS, HOOC or $H_2N$ groups optionally present in radicals $E^1$ and $E^2$ can be present in protected form. Details of possible protective group syntheses are further described below.

The production of compounds of general formula V takes place in that a feedstock of general formula VII

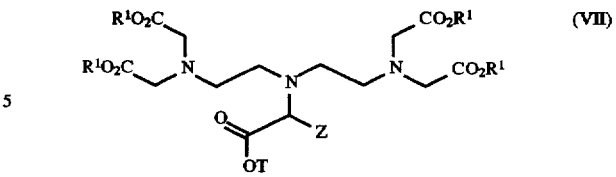

in which $R^1$ and Z have the above-indicated meaning and T can be a straight-chain or branched $C_1$–$C_6$ alkyl group, a benzyl, trimethylsilyl, triisopropylsilyl, 2,2,2-trifluoroethoxy, 2,2,2-trichloroethoxy group, or a metal ion equivalent of an alkali or alkaline-earth element, in which T is always different from $R^1$, is converted by cleavage of group T to the compound of general formula V. Preferred radical T is the benzyl radical, if $R^1$ stands for a tert-butyl group.

The cleavage of protective group T from compounds of general formula VII takes place according to the processes known to one skilled in the art, such as, for example, by hydrolysis, hydrogenolysis, acid or alkaline saponification of esters in aqueous-alkaline medium, and optionally solubilizers such as alcohols, preferably methanol, ethanol, isopropanol or ethers, such as tetrahydrofuran, 1,4-dioxane, 1,2-dimethoxyethane, can be added. Alkali or alkaline-earth hydroxides, or their carbonates, such as, e.g., lithium hydroxide, sodium hydroxide, barium hydroxide or potassium carbonate and cesium carbonate can be used as bases. Preferred temperatures are 0°–100° C., especially 0°–50° C. The subsequent isolation of the compound of general formula V takes place so that it is reacted with an ammonium salt, such as, e.g., $NH_4Cl$, $(NH_4)_2SO_4$ or $(NH_4)_3PO_4$, or the salts are converted to the free acids with acid ion exchanger.

Also, the use of diluted citric acid or acid ion exchanger has proven itself for the release of the acid function from alkali or alkaline-earth salts.

The acid saponification is performed with mineral acids, such as, e.g., hydrochloric acid, sulfuric acid or else also organic acids (e.g., trifluoroacetic acid) at temperatures of 0°–100° C., preferably 0°–50° C., in the case of trifluoroacetic acid between 0°–25° C. The cleavage of silyl-containing protective groups takes place by means of fluoride ions by the methods familiar to one skilled in the art.

The hydrogenolytic cleavage of benzyl derivatives takes place with use of the palladium catalysts known to one skilled in the art, preferably 10% Pd on activated carbon or Pearlman's catalyst $Pd(OH)_2$ on carbon. Homogeneous catalysts of the Wilkinson catalyst type can also be used. The hydrogenation is performed in alcohols such as methanol, ethanol or isopropanol, but preferably in isopropanol, at temperatures between 10°–50° C., but preferably at room temperature and normal pressure.

The production of compounds of general formula VII takes place, for example, in that an amino acid derivative of general formula VIII

in which T and Z have the above-indicated meaning, is reacted with an alkylating agent of general formula IX

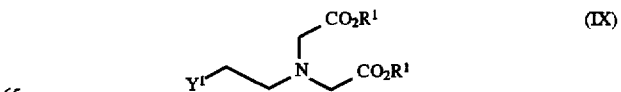

in which
$R^1$ has the above-indicated meaning, and $Y^1$ stands for a halogen atom such as Cl, Br or I, but preferably Cl (see also M. A. Williams, H. Rapoport, J. Org. Chem., 58, 1151 (1993)).

Preferred amino acid derivatives are the esters of naturally occurring 2-amino acids.

The reaction of compound (VIII) with compound (IX) takes place preferably in a buffered alkylation reaction, in which an aqueous phosphate buffer solution is used as buffer. The reaction takes place at pH 7–9, but preferably at pH 8. The buffer concentration can be between 0.1–2.5M, but a 2M phosphate-buffer solution preferably is used. The temperature of the alkylation can be between 0° and 50° C., the preferred temperature is room temperature.

The reaction is performed in a polar solvent, such as, e.g., acetonitrile, tetrahydrofuran, 1,4-dioxane or 1,2-dimethoxyethane. Acetonitrile is preferably used.

If $Y^1$ in general formula IX is a chlorine or bromine atom, an alkali iodide, such as, e.g., sodium iodide or potassium iodide, can be added to the reaction in catalytic amounts.

The amino acid esters of general formula VIII used in the reaction can be produced from the commercially available amino acids according to methods known to one skilled in the art (e.g., Houben-Weyl, Methoden der organischen Chemie, Synthese yon Peptiden [Synthesis of Peptides], Part II, Volume XV/2, Georg Thieme Verlag Stuttgart, 1974, p. 3 ff). As commercially available products, amino acids and derivatives can be obtained, e.g., with the Fluka Chemie [Fluka Chemistry]AG, CH-9470 Buchs or the BACHEM Feinchemikalien [BACHEM Fine Chemicals]AG, CH-4416 Bubendorf.

Preferred amino acid derivatives of general formula VIII are the amino acid benzyl esters. In the synthesis of these compounds, salts (such as, e.g., hydrochlorides, hydrosulfates, sulfates, phosphates or p-toluene sulfonates) generally accumulate, which can be used advantageously directly in the reaction.

The structural element of general formula IX used in the alkylation can be produced analogously to the description of Rapoport if $Y^1$=Br. But the corresponding compound with $Y^1$=Cl can be used in the same way for the above-described reaction. The chlorine compound can be produced economically, moreover, from the alcohol of general formula X

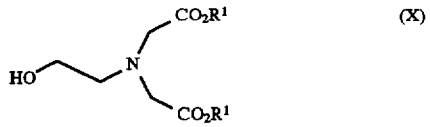

by reaction with thionyl chloride.

An alternative method for the production of compounds of general formula VII consists in that a compound of general formula XI

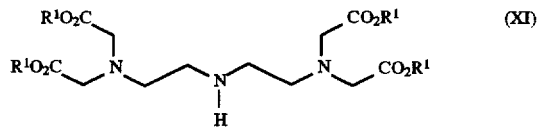

with
$R^1$ in the above-indicated meaning is reacted with an alkylating agent of general formula XII

in which

T and Z have the above-mentioned meaning and in which Nu stands for a nucleofuge, such as Cl, Br, I, p-$CH_3CeH_4SO_3$, $CH_3SO_3$, or $CF_3SO_3$, preferably for Br and Cl.

The reaction to the compound of general formula VII takes place in polar solvents, such as dimethylformamide, acetonitrile, tetrahydrofuran, 1,4-dioxane, formamide, dimethylacetamide, dimethyl sulfoxide, acetone, as well as in alcohols, such as, for example, methanol, ethanol, isopropanol, preferably in acetonitrile and dimethylformamide. In the case of the preferred bromides and chlorides, catalytic amounts of iodide can be added. For catching the acid that has developed in the alkylation, organic bases, such as, e.g., triethylamine, Hünig base or 1,4-diazabicyclooctane (DABCO), or else metal hydrides, for example sodium hydride or alkali or alkaline-earth hydroxides or their carbonates, are used. Preferably potassium carbonate is used. The reactions take place at 0°–100° C. preferably between 20° and 60° C. The alkylating reagents described by general formula XII are partially commercially available or can be produced from the corresponding carboxylic acids, or α-hydroxycarboxylic acids in a way known in the literature (see, for example: C. F. Ward, Soc., 121: 1164 (1922)).

The compound of general formula XI is obtained by cleavage of protective group A from the compound of general formula XIII

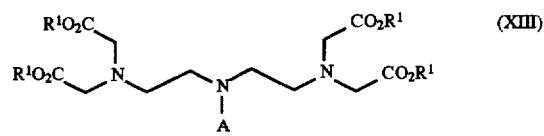

in which $R^1$ has the above-mentioned meaning and
A stands for a protective group, such as, for example, a benzyloxycarbonyl, tert-butyloxycarbonyl (BOC), fluorenylmethoxycarbonyl (FMOC), benzyl, 4-methoxybenzyl, $(CH_3)_3Si$—$(CH_2)_2$—$SO_2$, $CF_3CO$, $CCl_3CO$, $(C_6H_5)$(tert-Bu)$_2$Si or a trityl group.

The cleavage takes place, if A is the BOC radical, by treatment with trifluoroacetic acid. Silyl protective groups are cleaved with diluted mineral acid or with fluoride ions. If A means the $(CH_3)_3Si$—$(CH_2)_2$—$SO_2$ group, tetrabutylammonium fluoride is used as cleavage reagent. If A represents the benzyl radical or the benzyloxycarbonyl radical, the latter is cleaved by hydrogenolysis with palladium catalyst (10% Pd/C) or more advantageously with Pearlman's catalyst (Pd(OH)$_2$/C) in alcohol, preferably ethanol, at room temperature.

The compound of general formula XIII is obtained from the compound of general formula XIV

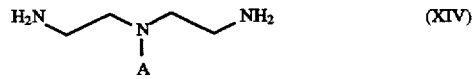

in which A has the above-mentioned meaning, by reaction with α-haloacetic acid esters.

The chloro- or bromoacetic acid-tert-butyl esters as well as the corresponding benzyl esters are preferably used. The reaction is conducted analogously to the reaction of the compound of general formula VIII with the compound of general formula IX to produce the compound of general formula VII.

The compound of general formula XIII, in which A represents the benzyl radical, can also be produced by reaction of benzylamine with the alkylating reagent general formula IX, as described above for the amino acid ester of general formula VIII.

The compound of general formula XIV is produced by a cleavage of protective group L, known to one skilled in the art, from the compound of general formula XV

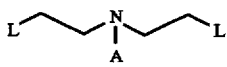 (XV)

in which
A has the above-mentioned meaning and in which
L stands for a group —NHD, in which
D represents, e.g., the benzyloxycarbonyl, BOC, CF$_3$CO, CCl$_3$CO or the trityl group
or
L stands for a phthalimido group.

If D stands for the benzyloxycarbonyl group, a hydrogenolysis takes place in the presence of palladium catalysts, as described above.

If D is the CF$_3$CO group, a saponification with alkali or alkaline-earth hydroxides or their carbonates, but preferably potassium carbonate, is performed. Ammonia water can also be used. As solvent, preferably mixtures of alcohols or tetrahydrofuran or 1,4-dioxane with water are used. The reaction temperatures are between 0°–60° C., the reaction is preferably performed at room temperature. If L is the phthalimino group, the cleavage of the phthalyl protective group takes place by hydrazinolysis or by treatment with alkali hydroxides, preferably sodium hydroxide or potassium hydroxide in aqueous alcohols, preferably n-butanol with refluxing or by treatment with aqueous mineral acids, preferably concentrated hydrochloric acid, with refluxing.

It has proven especially advantageous to undertake the saponification with aqueous potassium carbonate solution, since in this way, the alkylation to tetraesters of general formula XIII can be undertaken without isolating the intermediate stage of general formula XIV.

1,4,7-Triaza-4-benzyl-heptane can also be produced as described in EP 0292689.

The compound of general formula XV can be obtained by reaction of the compound of general formula XVI

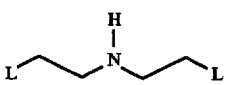 (XVI)

in which L has the above-indicated meaning with the standard protective group reagents (see, e.g., Protective Groups in Organic Syntheses, Second Edition, T. W. Greene and P. G. M. Wuts, John Wiley & Sons, Inc., New York, 1991).

The compounds of general formula XVI are obtained by reaction of an acylation reagent of general formula XVII

D-G (XVII)

with diethylenetriamine (XVIII)

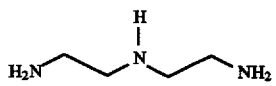 (XVIII)

in which
G stands for a C≡N group or an OR$^3$ group,
R$^3$ stands for a branched or unbranched, partially or completely fluorinated C$_1$–C$_6$ alkyl group or a benzyl group, or for the case that L represents the phthalimino group, D-G stands for phthalic anhydride.

In addition to the mentioned phthalic anhydride, preferred reagents D-G are trifluoroacetic acid ethyl ester and cyanobenzyl formate.

Thus, the reaction of diethylenetriamine (XVIII) with trifluoroacetic acid ethyl ester in ethanol at room temperature yields, in almost quantitative yield, the already known (U.S. Pat. No. 4,415,737 A (1983)) 1,7-bis-trifluoroacyl derivative (see Examples).

The 1,7-dibenzyloxycarbonyl compound (see Examples) can be obtained by reaction of diethylenetriamine (XV) with cyanobenzyl formate in tetrahydrofuran (Shun-Ichi Munehashi et al., Chemistry Letters, pp. 879–882 (1987)).

The phthalimido protective group can, as described in J. Org. Chem. USSR, 23: 3302 (1987), be introduced in diethylenetriamine.

Protective Groups

The protection of the designated groups in radicals E$^1$, E$^2$ and Z can take place with numerous possibilities known to one skilled in the art. The embodiments described below are used in explanation of these protective group techniques without being limited to these synthesis methods.

As acid protective groups, C$_1$–C$_6$ alkyl, C$_6$–C$_{10}$ aryl and C$_6$–C$_{10}$—Ar(C$_1$–C$_4$) alkyl groups as well as trialkylsilyl groups are suitable. Preferred are the methyl, ethyl, propyl, i-propyl, n-butyl, i-butyl and the tert-butyl group.

The cleavage of these acid protective groups takes place according to the processes known to one skilled in the art, for example, by hydrolysis, hydrogenolysis, alkaline saponification of esters with alkali in aqueous-alcoholic solution at temperatures of 0° to 50° C., acid saponification with mineral acids or in the case of tert-butyl esters with the help of trifluoroacetic acid.

As hydroxy protective groups, e.g., the benzyl, 4-methoxybenzyl, 4-nitrobenzyl, trityl, diphenylmethyl, trimethylsilyl, dimethyl-tert-butylsilyl, diphenyl-tert-butylsilyl groups are suitable.

The hydroxy groups can also be present, e.g., as THP-ethers, α-alkoxyethylethers, MEM ethers or as esters with aromatic or aliphatic carboxylic acids, such as, e.g., acetic acid or benzoic acid. In the case of polyols, the hydroxy groups can also be protected in the form of ketals with, e.g., acetone, acetaldehyde, cyclohexanone or benzaldehyde.

The hydroxy protective groups can be released according to the methods in literature known to one skilled in the art, e.g., by hydrogenolysis, acid treatment of the ethers and ketals or alkali treatment of esters (see, e.g., Protective Groups in Organic Syntheses, Second Edition, T. W. Greene and P. G. M. Wuts, John Wiley & Sons, Inc., New York, 1991).

The thiol groups can be protected as benzyl ethers, which can be cleaved with sodium in ammonia or boiling ethanol (W. I. Patterson, V. du Vigneaud, J. Biol. Chem. 111: 393, 1993). S-tert-butyl ethers are readily clearable with hydrogen fluoride/anisole at room temperature (S. Salzakibona et al., Bull. Chem. Soc. Japn., 40: 2164, (1967)). S-Benzyloxycarbonyl derivatives can be easily cleaved by concentrated ammonia at room temperature (A. Berger et al., J. Am. Chem. Soc., 78: 4483, 1956). Only at boiling temperature are S-benzyloxycarbonyl derivatives cleaved from trifluoroacetic acid (L. Zervas et al., J. Am. Chem. Soc., 85: 1337 (1963)).

The NH2 groups can be protected in varied ways and again opened. The N-trifluoroacetyl derivative is cleaved by potassium or sodium carbonate in water (H. Newman, J. Org. Chem., 30: 287 (1965), M. A. Schwartz et al., J. Am. Chem. Soc., 95, G12 (1973)) or simply by ammonia (M. Imazama and F. Eckstein, J. Org. Chem., 44: 2039 (1979)). The tert-butyloxycarbonyl derivative is equally easy to cleave: stirring with trifluoroacetic acid is sufficient (B. F. Lundt et al., J. Org. Chem., 43: 2285 (1978)).

The group of the NH$_2$ protective groups to be cleaved hydrogenolytically or reductively is very large: The N-benzyl group can be cleaved easily with hydrogen/Pd-C (W. H. Hartung and R. Simonoff, Org. Reactions VII, 263 (1953)), which also applies for the trityl group (L. Zervas et al., J. Am. Chem. Soc., 78: 1359 (1956)) and the benzyloxycarbonyl group (M. Bergmann and L. Zervas, Ber. 65: 1192 (1932)).

Of the silyl derivatives, the easily clearable tert-butyldiphenylsilyl compounds (L. E. Overman et al., Tetrahedron Lett. 27: 4391 (1986), as also the 2-(trimethylsilyl)-ethyl carbamates (L. Grehn et al., Angew. Chem. [Applied Chemistry] Int. Ed. Engl., 23: 296 (1983)) and the 2-trimethylsilylethanesulfonamides (R. S. Garigipati and S. M. Weinreb, J. Org. Chem., 53: 4143 (1988)) are used, which can be cleaved with fluoride ions.

Especially easily clearable is the 9-fluorenylmethylcarbamate: the cleavage takes place with amines, such as piperidine, morpholine, 4-dimethylaminopyridine, but also with tetrabutylammonium fluoride (L. A. Corpino et al., J. Org. Chem., 55: 1673 (1990), M. Ueki and M. Amemiya, Tetrahedron Lett., 28: 6617 (1987)).

Production and Use of the Agents According to the Invention

The production of the pharmaceutical agents according to the invention takes place in a way known in the art, for example, by the complexes or compounds according to the invention being suspended or dissolved in aqueous medium—optionally by adding the additives usual in galenicals—and then the suspension or solution optionally being sterilized. Suitable additives are, for example, physiologically harmless buffers (such as, for example, tromethamine), small additions of complexing agents (such as, for example, DTPA or the respective compounds of general formula I according to the invention with X meaning hydrogen) and/or their calcium, magnesium or zinc complexes or optionally electrolytes (such as, for example, sodium chloride) as well as antioxidants (such as, for example, ascorbic acid).

If suspensions or solutions of the agents according to the invention in water or physiological salt solution are desired for enteral administration or other purposes, they are mixed with one or more adjuvants usual in galenicals, such as, for example, methylcellulose, lactose or mannitol, and/or surfactants, such as, for example, lecithins, Tween® or Myrj®, and/or flavoring substances for taste correction, such as, for example, ethereal oils.

It is also possible, in principle, to produce the pharmaceutical agents according to the invention even without isolating the complex salts. In each case, special care must be used to undertake the complexing or chelation, so that the salts and salt solutions according to the invention are practically free of noncomplexed metal ions having a toxic effect.

This can be assured, for example, with the help of color indicators, such as xylenol orange, by control titrations during the production process. The invention therefore also relates to a process for the production of complex compounds and their salts. A purification of the isolated complex salt remains as a final precaution.

The pharmaceutical agents according to the invention preferably contain about 1 μmol/l to 2 mol/l of the complex salt and are preferably dosed in amounts of about 0.001–20 mmol/kg of body weight. They are intended for enteral and parenteral administration.

The complex compounds according to the invention are used:

1. for NMR diagnosis in the form of their complexes with divalent and trivalent ions of the elements of atomic numbers 21–29, 42, 44 and 57–70. Suitable preferred ions are, for example, the chromium(III), iron(II), cobalt(II), nickel(II), copper(II), praseodymium(III), neodymium(III), samarium(III) and ytterbium(III) ion. Because of their very strong magnetic moment, the gadolinium(III), terbium(III), dysprosium(III), holmium(III), erbium(III), manganese(II) and iron(III) ions are especially preferred.

2. for diagnostic radiology in the form of their complexes with an element of a higher atomic number, which assures a sufficient absorption of x rays. It has been found that complexes according to the invention, which contain elements of atomic numbers 57–83 as the central atom, are suitable for this application.

3. for radiodiagnosis and radiotherapy in the form of their complexes with radioactive central ions. Suitable are, for example, radioisotopes of the elements copper, cobalt, gallium, germanium, yttrium, holmium, lutetium, scandium, iron, europium, technetium, indium, ytterbium, gadolinium, samarium and iridium.

If X stands for one of the above-mentioned paramagnetic metals, the agents of general formula I according to the invention meet the varied requirements for suitability as contrast media for nuclear spin tomography. Thus, after oral or parenteral administration, they are excellently suited for improving the image, obtained with the help of the nuclear spin tomograph, in its informative value by increasing the signal intensity. Further, they show the high effectiveness that is necessary to load the body with the smallest possible amounts of foreign substances and the good compatibility, which is necessary to maintain the noninvasive nature of the examinations.

In general, the agents according to the invention for use as NMR diagnostic agents are dosed in amounts of preferably about 0.001–5 mmol/kg of body weight, more preferably about 0.005–0.5 mmol/kg of body weight. Details of such use are discussed, for example, in H. J. Weinmann et al., Am. J. of Roentgenology 142, 619 (1984).

Especially low dosages (under 1 mg/kg of body weight) of organ-specific NMR diagnostic agents can be used, for example, for detection of tumors and of myocardial infarction.

Further, the complex compounds according to the invention can advantageously be used as susceptibility reagents and as shift reagents for in vivo NMR spectroscopy.

In addition, the agents according to the invention are excellently suited as x-ray contrast media, and it is especially to be emphasized that no signs of the anaphylactic-type reactions in biochemical-pharmacological investigations, known from the iodine-containing contrast media, can be detected with them. The substances according to the invention meet the varied requirements, which are imposed on contrast media in modern diagnosis. The compounds and agents produced from them are distinguished by a high absorption coefficient for x rays, a good compatibility, a high effectiveness, a low viscosity, a low osmolality, an advantageous precipitation kinetics.

In addition to the surprisingly good compatibility of the heavy metal complexes, the compounds according to the invention in diagnostic radiology have a positive effect in that the complex compounds according to the invention especially also allow for investigations with shorter-wave x-ray radiation than that which is possible with conventional contrast media, by which the radiation exposure of the patient is clearly reduced, since, as is generally known, soft radiation of tissue is much more greatly absorbed than hard [R. Felix, "Das Röntgenbild [The X-Ray Image]"; Thieme-Verlag Stuttgart (1980)].

Because of the advantageous absorption properties of the contrast media according to the invention in the area of hard x-ray radiation, the agents are also especially suitable for digital substraction techniques (which work with higher tube voltages).

Details of the use of x-ray contrast media are discussed, for example, in Barke, Röntgenkontrastmittel [X-Ray Contrast Media], G. Thieme, Leipzig (1970) and P. Thurn, E. B ücheler "Einführung in die Röntgendiagnostik [Introduction in X-Ray Diagnosis]," G. Thieme, Stuttgart, New York (1977).

In general, the agents according to the invention are dosed for use as x-ray contrast media in amounts of preferably about 0.1–20 mmol/kg of body weight, more preferably about 0.25–5 mmol/kg of body weight.

If the agents according to the invention are radioactive, they are also suitable as radiodiagnostic agents because of their advantageous properties and the good stability of the complex compounds contained in them. Details of their use and dosage are described, e.g., in "Radiotracers for Medical Applications," CRC Press, Boca Raton, Fla.

Another imaging method with radioisotopes is the positron emission tomography, which uses positron-emitting isotopes, such as, e.g., $^{43}$Sc, $^{44}$Sc, $^{52}$Fe, $^{55}$Co and $^{66}$Ga [Heiss, W. D.; Phelps, M. E.; Positron Emission Tomography of the Brain, Springer-Verlag Berlin, Heidelberg, New York (1983)].

The compounds according to the invention can also be used in radioimmunotherapy or radiation therapy. The latter is distinguished from the corresponding diagnosis only by the amount and type of the isotope used. In this case, the object is the destruction of tumor cells by high-energy shortwave radiation with a smallest possible range of action. Suitable β-emitting ions are, e.g., $^{46}$Sc, $^{47}$Sc, $^{48}$Sc, $^{72}$Ga, $^{73}$Ga and $^{90}$. Suitable α-emitting ions exhibiting small half-lives are, e.g., $^{211}$Bi, $^{212}$Bi, $^{213}$Bi, $^{214}$Bi, and $^{212}$Bi is preferred. A suitable photon- and electron-emitting ion is $^{158}$Gd, which can be obtained from $^{157}$Gd by neutron capture.

If the agent according to the invention is intended for use in the variant of radiation therapy proposed by R. L. Mills et al. [Nature Vol. 336, (1988), p. 787), the central ion must be derived from a Mössbauer isotope, such as, for example, $^{57}$Fe or $^{151}$Eu.

Details of the use of radiotherapeutic agents are discussed, e.g., in R. W. Kozak et al., TIBTEC, October 1986, 262.

The administration of aqueous x-ray and NMR contrast medium solutions can take place enterally or parenterally, namely orally, rectally, intravenously, intraarterially, intravascularly, intracutaneously, subcutaneously (lymphography), subarachnoidally (myelography), and the intravenous administration is preferred.

The agents according to the invention exhibit not only a high stability in vitro, but also a surprisingly high stability in vivo, so that a release or an exchange of ions—toxic in themselves—not covalently bound to the complexes does not take place within the time in which the new contrast media are completely excreted again.

In general, it has been possible to synthesize new complexing agents, metal complexes and metal complex salts, which open up new possibilities in diagnostic and therapeutic medicine. The invention therefore relates to the above-explained compounds of general formula I, process for their production, pharmaceutical agents, process for the production of these agents and the use of these agents in diagnosis and therapy.

The entire disclosure of all applications, patents and publications, cited above and below, including German Application No. 195 07 822.5, is hereby incorporated by reference.

The following examples are used for a more detailed explanation of the object of the invention without intending to be limited to this object.

The following examples are used for a more detailed explanation of the object of the invention without intending to be limited to this object.

EXAMPLES

Example 1

3,9-Bis(tert-butoxycarbonylmethyl)-3,6,9-triazaundecanedioic acid-di-tert-butyl ester a) 1,7-Bis(trifluoroacetyl)-1,4,7-triazaheptane 113.3 g (790 mmol) of trifluoroacetic acid ethyl ester is instilled in a solution of 41.14 g (390 mmol) of 1,4,7-triazaheptane in 350 ml of tetrahydrofuran at 0° C. and under nitrogen. It is allowed to stir overnight at room temperature, concentrated by evaporation in a vacuum. The remaining oil is crystallized from hexane.

Yield: 115 g (99.9% of theory) Melting point: 68°–70° C. Elementary analysis: Cld: C 32.55 H 3.76 F 38.62 N 14.24 Fnd: C 32.63 H 3.75 F 38.38 N 14.19 b) 1,7-Bis(trifluoroacetyl)-4-benzyloxycarbonyl-1,4,7-triazaheptane 14.75 g (50 mmol) of the trifluoroacetyl compound produced under Example 1a) as well as 8.3 ml (60 mmol) of triethylamine are dissolved in 120 ml of dichloromethane and cooled to 0° C. 7.5 ml (53 mmol) of benzyl chloroformate (97%), dissolved in 20 ml of dichloromethane, is now instilled with stirring. It is allowed to stir overnight at room temperature, the salts are extracted with distilled water, the dichloromethane solution is dried on sodium sulfate, evaporated to dryness in a vacuum and the residue is crystallized from ether/hexane.

Yield: 18.40 g (85.7% of theory) Melting point: 131°–32° C. Elementary analysis: Cld: C 44.76 H 3.99 F 26.55 N 9.79 Fnd: C 44.87 H 4.03 F 26.62 N 9.61 c) 3,9-Bis(tert-butoxycarbonylmethyl)-6-benzyloxycarbonyl-3,6,9-triazaundecanedicarboxylic acid-di-tert-butyl ester 4.29 g (10 mmol) of the trifluoroacetyl derivative produced under Example 1b) is dissolved in 30 ml of ethanol and mixed with 800 mg (20 mmol) of sodium hydroxide solution in 10 ml of distilled water. It is stirred for 3 hours at room temperature, evaporated to dryness in a vacuum at 40° C. bath temperature, water residues are removed by azeotropic distillation with isopropanol and taken up in 30 ml of dimethylformamide. Then, 6.9 g (50 mmol) of potassium carbonate as well as 9.7 g (50 mmol) of bromoacetic acid-tert-butyl ester are added to it and the 4-benzyloxycarbonyl-1,4,7-triazaheptane is alkylated at room temperature overnight. The dimethylformamide is then drawn off in an oil pump vacuum, the residue is dispersed between water and dichloromethane, the organic solution is dried on sodium sulfate, evaporated to dryness in a vacuum and the residue is purified by chromatography on silica gel. The title compound is eluted with ethyl acetate/hexane. It is obtained as foam.

Yield: 6.49 g (93.6% of theory) Elementary analysis: Cld: C 62.32 H 8.57 N 6.06 Fnd: C 62.41 H 8.66 N 6.01 d) 3,9-Bis(tert-butoxycarbonylmethyl)-3,6,9-triazaundecanedicarboxylic acid-di-tert-butyl ester 3.5 g (5 mmol) of the compound produced under Example 1c) is dissolved in 100 ml of ethanol, mixed with 200 mg of Pearlman's catalyst (Pd 20% on activated carbon) and hydrogenated until the calculated amount of hydrogen is taken up. It is suctioned off from the catalyst and evaporated to dryness in a vacuum. The title compound is obtained as white foam.

Yield: 2.80 g (99.9% of theory) Elementary analysis: Cld: C 60.08 H 9.54 N 7.51 Fnd: C 60.02 H 9.62 N 7.56 e) 3,9-Bis(tert-butoxycarbonylmethyl)-6-(2-methyl) ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 2.17 g (12 mmol) of 2-bromopropionic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.18 g (63.4% of theory) Elementary analysis: Cld: C 60.07 H 9.32 N 6.37 Fnd: C 60.18 H 9.40 N 6.31 f) 3,9-Bis(tert-butoxycarbonylmethyl)-6-(2-methyl) carboxymethyl-3,6,9-triazaundecanedioic acid-di-tert-butyl ester 6.60 g (10 mmol) of the compound produced under Example 1e) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained as foam.

Yield: 5.35 g (84.7% of theory) Elementary analysis: Cld: C 58.93 H 9.09 N 6.65 Fnd: C 59.01 H 9.16 N 6.60 g) 3,9-Bis(tert-butoxycarbonylmethyl)-6-(2-methyl) decylaminocarbonylmethyl-3,6,9-triazaundecanedioic acid-di-tert-butyl ester 5.00 g (7.91 mmol) of the title compound of Example 1f) is dissolved in 25 ml of dimethylformamide, and 1.00 g (8.70 mol) of N-hydroxysuccinimide is added. It is cooled off to 0° C. and 1.795 g (8.7 mmol) of dicyclohexylcarbodiimide is added. It is stirred for one hour at 0° C. and then for 4 hours at room temperature. It is cooled off to 0° C. and a solution of 1.25 g of decylamine (7.91 mmol) in 10 ml of dimethylformamide is instilled within 10 minutes. It is stirred for one hour at 0° C., then overnight at room temperature. It is evaporated to dryness in a vacuum and the residue is taken up in 100 ml of ethyl acetate. It is filtered off from precipitated urea and the filtrate is washed twice with 100 ml each of 5% aqueous soda solution. The organic phase is dried on magnesium sulfate and evaporated to dryness in a vacuum. The residue is chromatographed on silica gel (mobile solvent: n-hexane/ethyl acetate 20:1). 5.31 g (87% of theory) of a colorless oil is obtained.

Elementary analysis: Cld: C 63.86 H 10.20 N 7.27 Fnd: C 63.95 H 10.28 N 7.18 h) 3,9-Bis(carboxymethyl)-6-(2-methyl) decylaminocarbonylmethyl-3,6,9-triazaundecanedioic acid 5 g (6.48 mmol) of the title compound of Example 1g) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 ($H^+$form) is added and stirred for 10 minutes at room temperature. It is filtered off from the ion exchanger and evaporated to dryness in a vacuum.

Yield: 2.34 g (61% of theory) of a vitreous solid Water content: 7.5% Elementary analysis (relative to anhydrous substance): Cld: C 54.93 H 8.48 N 10.25 Fnd: C 54.85 H 8.55 N 10.17 i) Gadolinium complex of 3,9-bis(carboxymethyl)-6-(2-methyl)-decylaminocarbonylmethyl-3,6,9-triazaundecanedioic acid-monosodium salt 5.0 g (9.14 mmol) of the title compound of Example 1h) is dissolved in 50 ml of deionized water and mixed at room temperature in portions with 1.65 g (4.57 mmol) of gadolinium oxide. After a reaction time of 3 hours at 80° C., the now almost clear reaction solution is cooled off to room temperature and adjusted with 1N sodium hydroxide solution to pH 7.2. After filtration, the obtained filtrate is freeze-dried.

Yield: 6.48 g (98.2% of theory) of an amorphous powder Water content: 5.62%

Elementary analysis (relative to anhydrous substance): Cld: C 41.54 H 5.86 N 7.75 Gd 21.75 Na 3.18 Fnd: C 41.48 H 5.80 N 7.69 Gd 21.68 Na 3.11 j) Iron complex of 3,9-bis(carboxymethyl)-6-(2-methyl) decylaminocarbonylmethyl-3,6,9-triazaundecanedioic acid-monosodium salt 2.0 g (3.65 mmol) of the title compound of Example 1h) is dissolved in 100 ml of deionized water and mixed at 80° C. in portions with 1.29 g (3.65 mmol) of iron(III)-acetylacetonate. After a reaction time of 2 hours at 80° C., the now yellow-colored reaction solution is cooled off to room temperature and extracted twice with 50 ml of methylene chloride in each case. Then, a pH of 7.2 is set by salinization of the aqueous product solution with 1N sodium hydroxide solution. After filtration, the obtained filtrate is freeze-dried.

Yield: 2.2 g (97.4% of theory) of an amorphous powder Elementary analysis (relative to anhydrous substance):

Cld: C 48.32 H 6.81 N 9.02 Fe 8.99 Na 3.70 Fnd: C 48.36 H 6.82 N 9.10 Fe 9.02 Na 3.74

Example 2

3,9-Bis(tert-butoxycarbonylmethyl)-6-(2-benzyl) carboxymethyl-3,6,9-triazaundecanedioic acid-di-tert-butyl ester a) 1,7-Bis(benzyloxycarbonyl)-1,4,7-triazaheptane 4.87 g (47.2 mmol) of 1,4,7-triazaheptane as well as 5 ml of triethylamine are dissolved in 100 ml of dichloroethane. The solution of 15.22 g (94.4 mmol) of cyanobenzyl formate in 200 ml of dichloromethane is instilled in this solution within 3 hours. It is allowed to stir for 2 more days at room temperature, then evaporated to dryness in a vacuum, taken up in diethyl ether and washed with sodium bicarbonate solution. The ether solution is dried on sodium sulfate and evaporated to dryness in a vacuum. The residue is crystallized from a little ethanol. The title compound crystallizes into white needles.

Yield: 11.46 g (65.7% of theory) Melting point: 73°–75° C. Elementary analysis: Cld: C 64.67 H 6.78 N 11.31 Fnd: C 64.82 H 6.64 N 11.28 b) 1,7-Bis(benzyloxycarbonyl)-4-trifluoroacetyl-1,4,7-triazaheptane

Analogously to Example 1a), 37.14 g (100 mmol) of the amino compound produced under Example 2a is reacted with 15.63 g (110 mmol) of trifluoroacetic acid ethyl ester in 100 ml of tetrahydrofuran and worked up. The title compound is obtained as oil.

Yield: 43.57 g (93.2% of theory) Elementary analysis: Cld: C 56.53 H 5.18 F 12.19 N 8.99 Fnd: C 56.60 H 5.24 F 12.14 N 9.04 c) 3,9-Bis(tert-butoxycarbonylmethyl)-6-trifluoroacetyl-3,6,9-triazaundecanedioic acid-di-tert-butyl ester Analogously to Example 1d), 4.675 g (10 mmol) of the trifluoroacetyl compound, produced under Example 5f), in 100 ml of ethanol is hydrogenated with 0.5 g of Pearlman's catalyst (Pd 20%, C) to 4-trifluoroacetyl-1,4,7-triazaheptane and worked up. The amino compound is then alkylated according to Example 1e) in 30 ml of dimethylformamide with 9.7 g (50 mmol) of bromoacetic acid-tert-butyl ester in the presence of 6.9 g (50 mmol) of potassium carbonate. The working-up and purification of the title compound also takes place analogously to 5c).

Yield: 5.88 g (89.6% of theory) Elementary analysis: Cld: C 54.95 H 7.99 F 8.69 N 6.41 Fnd: C 54.90 H 8.05 F 8.62 N 6.36 d) 3,9-Bis(tert-butoxycarbonylmethyl)-3,6,9-triazaundecanedicarboxylic acid-di-tert-butyl ester Analogously to Example 1c), 6.57 g (10 mmol) of the trifluoroacetyl compound, produced under Example 2c), is dissolved in 50 ml of ethanol and saponified with 400 mg (10 mmol) of sodium hydroxide solution. It is concentrated by evaporation, the amino compound is taken up in warm toluene, washed with a little water, dried on sodium sulfate and evaporated to dryness in a vacuum. The title compound is obtained as foam.

Yield: 5.24 g (93.6% of theory) Elementary analysis (relative to anhydrous substance): Cld: C 60.08 H 9.54 N 7.51 Fnd: C 60.02 H 9.48 N 7.44 e) 3,9-Bis(tert-butoxycarbonylmethyl)-6-(2-benzyl)-ethoxycarbonylmethyl-3,6,9-triazaundecanedioic acid-di-tert-butyl ester 5.60 g (10 mmol) of the amino compound produced under Example 2d) is dissolved in 30 ml of dimethylformamide. Then, 1.66 g (12 mmol) of potassium carbonate as well as 3.0 g (12 mmol) of 2-bromophenylpropionic acid ethyl ester are added to it at room temperature and stirred overnight. It is then poured on ice water, extracted with ethyl acetate, the organic solution is dried on sodium sulfate, evaporated to dryness in a vacuum, and the title compound is obtained by chromatography on silica gel. A mixture of ethyl acetate/hexane is used as eluant.

Yield: 4.30 g (58.4% of theory) Elementary analysis: Cld: C 64.65 H 9.00 N 5.95 Fnd: C 64.62 H 9.07 N 5.90 f) 3,9-Bis(tert-butoxycarbonylmethyl)-6-(2-benzyl)-carboxymethyl-3,6,9-triazaundecanedioic acid-di-tert-butyl ester 7.06 g (10 mmol) of the compound produced under Example 2e) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions are taken up in butanol and evaporated to dryness again in a vacuum. The residue is extracted with toluene. The organic solution is evaporated to dryness in a vacuum and the title compound is obtained as foam.

Yield: 6.03 g (85.2% of theory) Elementary analysis: Cld: C 63.79 H 8.77 N 6.20 Fnd: C 63.68 H 8.83 N 6.26 g) 3,9-Bis(tert-butoxycarbonylmethyl)-6-(2-benzyl)pentylaminocarbonylmethyl-3,6,9-triazaundecanedioic acid-di-tert-butyl ester 5.00 g (7.91 mmol) of the title compound of Example 2f) is dissolved in 25 ml of dimethylformamide, and 894 mg (7.77 mol) of N-hydroxysuccinimide is added. It is cooled off to 0° C. and 1.603 g (7.77 mmol) of dicyclohexylcarbodiimide is added. It is stirred for one hour at 0° C. and then for 4 hours at room temperature. It is cooled off to 0° C. and a solution of 0.62 g of pentylamine (7.06 mmol) in 10 ml of dimethylformamide is instilled within 10 minutes. It is stirred for one hour at 0° C., then overnight at room temperature. It is evaporated to dryness in a vacuum and the residue is taken up in 100 ml of ethyl acetate. It is filtered off from precipitated urea and the filtrate is washed twice with 100 ml each of 5% aqueous soda solution. The organic phase is dried on magnesium sulfate and evaporated to dryness in a vacuum. The residue is chromatographed on silica gel (mobile solvent: n-hexane/ethyl acetate 20:1). 4.77 g (87% of theory) of a colorless oil is obtained.

Elementary analysis (relative to anhydrous substance): Cld: C 64.92 H 9.34 N 7.21 Fnd: C 64.81 H 9.28 N 7.25 h) 3,9-Bis(carboxymethyl)-6-(2-benzyl)-pentylaminocarbonylmethyl-3,6,9-triazaundecanedioic acid 4.50 g (5.79 mmol) of the title compound of Example 2g) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 ($H^+$ form) is added and stirred for 10 minutes at room temperature. It is filtered off from the ion exchanger and evaporated to dryness in a vacuum.

Yield: 2.28 g (67% of theory) of a vitreous solid Water content: 6.1% Elementary analysis (relative to anhydrous substance): Cld: C 56.51 H 7.30 N 10.14 Fnd: C 56.61 H 7.22 N 10.03 i) Gadolinium complex of 3,9-bis(carboxymethyl)-6-(2-benzyl)-pentylaminocarbonylmethyl-3,6,9-triazaundecanedioic acid-monosodium salt Analogously to Example 1i), after freeze-drying, the reaction of 2.5 g (4.52 mmol) of the title compound of Example 2h) with 0.82 g (2.26 mmol) of gadolinism oxide yields 3.24 g (98.4% of theory) of the title compound as amorphous powder.

Water content: 6.38% Elementary analysis (relative to anhydrous substance): Cld: C 42.85 H 4.98 N 7.69 Gd 21.58 Na 3.15 Fnd: C 42.78 H 4.96 N 7.68 Gd 21.52 Na 3.09 j) Dysprosium complex of 3,9-Bis(carboxymethyl)-6-(2-benzyl)-pentylaminocarbonylmethyl-3,6,9-triazaundecanedioic acid-monosodium salt 4.0 g (7.23 mmol) of the title compound of Example 2h) is dissolved in 60 ml of deionized water and mixed at room temperature in portions with 1.35 g (3.62 mmol) of dysprosium oxide. After a reaction time of 3 hours at 80° C., the now almost clear reaction solution is cooled to room temperature and a pH of 7.2 is set with 1N sodium hydroxide solution. After filtration, the obtained filtrate is freeze-dried.

Yield: 5.13 g (96.8% of theory) of an amorphous powder Water content: 7.43% Elementary analysis (relative to anhydrous substance): Cld: C 42.54 H 4.94 N 7.63 Dy 22.14 Na 3.13 Fnd: C 42.60 H 4.98 N 7.64 Dy 22.19 Na 3.16

Example 3

3,9-Bis(tert-butoxycarbonylmethyl)-6-(2-isopropyl)-carboxymethyl-3,6,9-triazaundecanedioic acid-di-tert-butyl ester a) 1,7-Bis(trifluoroacetyl)-4-benzyl-1,4,7-triazaheptane 29.52 g (100 mmol) of the bis(trifluoroacetyl) compound produced under Example 1a) is dissolved in 200 ml of dimethylformamide. Then, 16.6 g (120 mmol) of potassium carbonate as well as 20.53 g (120 mmol) of benzyl bromide are added to it at room temperature and stirred overnight. Then, it is diluted with 500 ml of diethyl ether, suctioned off from the salts, the ether is drawn off in a vacuum and then concentrated by evaporation in an oil pump vacuum to 50 ml. It is diluted with 600 ml of diethyl ether, poured on ice water and the organic solution is taken up, dried on sodium sulfate, evaporated to dryness in a vacuum and the title compound is obtained by chromatography on silica gel. A mixture of ethyl acetate/hexane is used as eluant.

Yield: 317.50 g (82.4% of theory) Elementary analysis: Cld: C 46.76 H 4.45 F 29.58 N 10.91 Fnd: C 46.83 H 4.51 F 29.50 N 10.87 b) 3,9-Bis(tert-butoxycarbonylmethyl)-6-benzyl-3,6,9-triazaundecanedicarboxylic acid-di-tert-butyl ester 38.53 g (100 mmol) of the trifluoroacetyl derivative produced under 3a) is dissolved in 300 ml of ethanol and mixed with 8 g (200 mmol) of sodium hydroxide solution in 100 ml of distilled water. It is stirred for 3 hours at room temperature, evaporated to dryness in a vacuum at 50° C. bath temperature, water residues are removed by azeotropic distillation with isopropanol and taken up in 300 ml of dimethylformamide. Then, 69 g (500 mmol) of potassium carbonate as well as 97 g (500 mmol) of bromoacetic acid-tert-butyl ester are added to it and the 4-benzyl-1,4,7-triazaheptane is alkylated at room temperature overnight. Then, the dimethylformamide is drawn off in an oil pump vacuum, the residue is dispersed between water and dichloromethane, the organic solution is dried on sodium sulfate, evaporated to dryness in a vacuum and the residue is purified by chromatography on silica gel. The title compound is eluted with ethyl acetate/hexane. It is obtained as foam.

Yield: 59.85 g (92.1% of theory) Elementary analysis: Cld: C 64.69 H 9.15 N 6.47 Fnd: C 64.75 H 9.23 N 6.44 c) 3,9-Bis(tert-butoxycarbonylmethyl)-3,6,9-triazaundecanedicarboxylic acid-di-tert-butyl ester 6.50 g (10 mmol) of the compound produced under 3b) is dissolved in 100 ml of ethanol, mixed with 400 mg of Pearlman's catalyst (Pd 20%, C) and hydrogenated until 224 ml of hydrogen is taken up. It is suctioned off from the catalyst, rewashed with ethanol and evaporated to dryness in a vacuum. The title compound is obtained as white foam.

Yield: 5.58 g (99.5% of theory) Elementary analysis: Cld: C 60.08 H 9.54 N 7.51 Fnd: C 60.17 H 9.60 N 7.57 d) 3,9-Bis(tert-butoxycarbonylmethyl)-6-(2-isopropyl)ethoxycarbonylmethyl-3,6,9-triazaundecanedioic acid-di-tert-butyl ester 5.60 g (10 mmol) of the amino compound produced under Example 3c) is dissolved in 30 ml of dimethylformamide. Then, 1.66 g (12 mmol) of potassium carbonate as well as 2.0 g (12 mmol) of 2-bromo-2-isopropylacetic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.07 g (59.2% of theory) Elementary analysis: Cld: C 61.11 H 9.52 N 6.11 Fnd: C 61.03 H 9.60 N 6.17 e) 3,9-Bis(tert-butoxycarbonylmethyl)-6-(2-isopropyl)-carboxymethyl-3,6,9-triazaundecanedioic acid-di-tert-butyl ester 6.88 g (10 mmol) of the compound produced under Example 3d) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained from hexane.

Yield: 5.53 g (83.8% of theory) Elementary analysis: Cld: C 60.07 H 9.32 N 6.37 Fnd: C 60.18 H 9.41 N 6.44 f) 3,9-Bis(tert-butoxycarbonylmethyl)-6-(2-isopropyl)-N-morpholinocarbonylmethyl-3,6,9-triazaundecanedioic acid-di-tert-butyl ester 5 g (7.58 mmol) of the title compound of Example 3e) and 660 mg (7.58 mmol) of morpholine are dissolved in 30 ml of toluene and 2.06 g (8.34 mmol) of 2-ethoxy-1-ethoxycarbonyl-1,2-dihydroquinoline is added at 0° C. It is stirred for 30 minutes at 0° C., then overnight at room temperature. It is evaporated to dryness in a vacuum and the residue is chromatographed on silica gel (mobile solvent: hexane/ethyl acetate =15:1).

Yield: 5.14 g (93% of theory) of a colorless oil Elementary analysis: Cld: C 60.96 H 9.40 N 7.69 Fnd: C 60.87 E 9.51 N 7.60 g) 3,9-Bis(tert-carboxymethyl)-6-(2-isopropyl)-N-morpholinocarbonylmethyl-3,6,9-triazaundecanedioic acid 5.00 g (6.86 mmol) of the title compound of Example 3f) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 (H$^+$ form) is added and stirred for 10 minutes at room temperature. It is filtered off from the ion exchanger and evaporated to dryness in a vacuum.

Yield: 2.59 g (71% of theory) of a vitreous solid Water content: 5.3% Elementary analysis (relative to anhydrous substance): Cld: C 49.99 H 7.19 N 11.11 Fnd: C 49.85 H 7.25 N 11.03 h) Gadolinium complex of 3,9-bis(tert-carboxymethyl)-6-(2-isopropyl)-N-morpholinocarbonylmethyl-3,6,9-triazaundecanedioic acid-monosodium salt Analogously to Example 1i), after freeze-drying, the reaction of 3.0 g (5.94 mmol) of the title compound of Example 3g) with 1.07 g (2.97 mmol) of gadolinium oxide yields 5.48 g (98.4% of theory) of the title compound as amorphous powder.

Water content: 4.94Elementary analysis (relative to anhydrous substance): Cld: C 37.05 H 4.74 N 8.23 Gd 23.10 Na 3.38 Fnd: C 37.09 H 4.76 N 8.26 Gd 23.12 Na 3.40 i) Europium complex of 3,9-bis(tert-carboxymethyl)-6-(2-isopropyl)-N-morphotinocarbonylmethyl-3,6,9-triazaundecanedioic acid-monosodium salt 2.5 g (4.95 mmol) of the title compound of Example 3g) is dissolved in 50 ml of deionized water and mixed at room temperature in portions with 0.87 g (2.47 mmol) of europium oxide. After a reaction time of 3 hours at 80° C., the now almost clear reaction solution is cooled off to room temperature and a pH of 7.2 is set with 1N sodium hydroxide solution. After filtration, the obtained filtrate is freeze-dried.

Yield: 3.25 g (97.5% of theory) of an amorphous powder Water content: 6.21% Elementary analysis (relative to anhydrous substance): Cld: C 37.34 H 4.78 N 8.29 Eu 22.50 Na 3.40 Fnd: C 37.21 H 4.69 N 8.19 Eu 22.24 Na 3.33

Example 4

3,9-Bis(tert-butoxycarbonylmethyl)-6-(2-phenyl) carboxymethyl-3,6,9-triazaundecanedioic acid-di-tert-butyl ester a) 1,7-Bis(phthalimido)-4-benzyl-1,4,7-triazaheptane 36.34 g (100 mmol) of 1,7-bis(phthalimido)-1,4,7-triazaheptane [produced according to J. Org. Chem. USSR, 23: 3302 (1987)]is dissolved in 500 ml of dimethylformamide. Then, 16.6 g (120 mmol) of potassium carbonate as well as 20.53 g (120 mmol) of benzyl bromide are added to it and stirred overnight at 25° C. It is poured in ice water, the precipitated product is suctioned off, rewashed with water, taken up in 1,2-dichloroethane, dried on sodium sulfate and evaporated to dryness in a vacuum. The title compound is obtained as solid.

Yield: 42.76 g (94.3% of theory) Elementary analysis: Cld: C 71.51 H 5.11 N 9.27 Fnd: C 71.40 H 5.18 N 9.38 b) 3,9-Bis(tert-butoxycarbonylmethyl)-6-benzyl-3,6,9-triazaundecanedioic acid-di-tert-butyl ester 22.68 g (50 mmol) of the compound produced under 4a) is added in portions with stirring in 250 ml of hydrazine hydrate. It is heated for 4 more hours to 60° C., allowed to cool off, suctioned off from phthalhydrazide, rewashed with hydrazine hydrate and concentrated by evaporation in a vacuum. The residue is freed from hydrazine residues by codistillation with isopropanol. The 4-benzyl-1,4,7-triazaheptane is taken up in 150 ml of dimethylformamide, 34.5 g (250 mmol) of potassium carbonate is added to it and finally 48.5 g (250 mmol) of bromoacetic acid-tert-butyl ester. The alkylation is allowed to be in progress overnight at room temperature. Then, the dimethylformamide is drawn off in an oil pump vacuum, the residue is dispersed between water and dichloromethane, dried on sodium sulfate, evaporated to dryness in a vacuum and the residue is purified by chromatography on silica gel. The title compound is obtained as foam.

Yield: 51.15 g (78.7% of theory) Elementary analysis: Cld: C 64.69 H 9.15 N 6.47 Fnd: C 64.60 H 9.20 N 6.53 c) 3,9-Bis(tert-butoxycarbonylmethyl)-3,6,9-triazaundecanedicarboxylic acid-di-tert-butyl ester 13.0 g (20 mmol) of the compound produced under 4b) is dissolved in 200 ml of ethanol, mixed with 0.8 g of Pearlman's catalyst (Pd 20%, C) and hydrogenated until 448 ml of hydrogen is taken up. It is suctioned off from the catalyst, rewashed with ethanol and evaporated to dryness in a vacuum. The title compound is obtained as foam.

Yield: 5.52 g (98.7% of theory) Elementary analysis: Cld: C 60.08 H 9.54 N 7.51 Fnd: C 60.01 H 9.62 N 7.58 d) 3,9-Bis(tert-butoxycarbonylmethyl)-6-(2-phenyl)-methoxycarbonylmethyl-3,6,9-triazaundecanedioic acid-di-tert-butyl ester 5.60 g (10 mmol) of the amino compound produced under Example 4c) is dissolved in 30 ml of dimethylformamide. Then, 1.66 g (12 mmol) of potassium carbonate as well as 2.22 g (12 mmol) of 2-chlorophenylacetic acid methyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.40 g (62.1% of theory) Elementary analysis: Cld: C 62.78 H 8.69 N 5.94 Fnd: C 62.89 H 8.76 N 5.88 e) 3,9-Bis(tert-butoxycarbonylmethyl)-6-(2-phenyl) carboxymethyl-3,6,9-triazaundecanedioic acid-di-tert-butyl ester 7.08 g (10 mmol) of the compound produced under Example 4d) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol, and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained as foam.

Yield: 5.99 g (86.3% of theory) Elementary analysis: Cld: C 62.32 H 8.57 N 6.06 Fnd: C 62.40 H 8.65 N 6.02 f) 3,9-Bis(tert-butoxycarbonylmethyl)-6-(2-phenyl)-(6'-hydroxyhexyl)-aminocarboxymethyl-3,6,9-triazaundecanedioic acid-di-tert-butyl ester 5 g (7.21 mmol) of the title compound of Example 4e) and 845 mg (7.21 mmol) of 6-aminohexan-1-ol are dissolved in 30 ml of toluene and 1.96 g (7.93 mmol) of 2-ethoxy-1-ethoxycarbonyl-1,2-dihydroquinoline is added at 0° C. It is stirred for 30 minutes at 0° C., then overnight at room temperature. It is evaporated to dryness in a vacuum and the residue is chromatographed on silica gel (mobile solvent: hexane/isopropanol=20:1). 4.52 g (79% of theory) of a colorless oil is obtained.

Elementary analysis: Cld: C 63.61 H 9.15 N 7.06 Fnd: C 63.75 H 9.27 N 6.95

3,9-Bis(carboxymethyl)-6-(2-phenyl)-(6'-hydroxyhexyl)-aminocarbonylmethyl-3,6,9-triazaundecanedioic acid 4 g (5.04 mmol) of the title compound of Example 4f) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 16 ml of acid ion exchanger IR 120 ($H^+$ form) is added and stirred for 10 minutes at room temperature. It is filtered off from the ion exchanger and evaporated to dryness in a vacuum.

Yield: 2.22 g (73% of theory) of a vitreous solid Water content: 5.8% Elementary analysis (relative to anhydrous substance): Cld: C 54.92 H 7.09 N 9.85 Fnd: C 54.87 H 7.18 N 9.77 h) Gadolinium complex of 3,9-bis(carboxymethyl)-6-(2-phenyl)-(6'-hydroxyhexyl)-aminocarbonylmethyl-3,6,9-triazaundecanedioic acid-monosodium salt Analogously to Example 1i), after freeze-drying, the reaction of 4.2 g (7.38 mmol) of the title compound of Example 4g) with 1.33 g (3.69 mmol) of gadolinium oxide yields 5.40 g (98.4% of theory) of the title compound as amorphous powder.

Water content: 7.56% Elementary analysis (relative to anhydrous substance): Cld: C 41.93 H 4.87 N 7.52 Gd 21.11 Na 3.09 Fnd: C 42.01 H 4.92 N 7.54 Gd 21.20 Na 3.12 i) Manganese complex of 3,9-bis(carboxymethyl)-6-(2-phenyl)-(6'-hydroxyhexyl)-aminocarbonylmethyl-3,6,9-triazaundecanedioic acid-disodium salt 3.0 g (5.27 mmol) of the title compound of Example 4g) is dissolved in 100 ml of deionized water and mixed at room temperature in portions with 0.60 g (5.27 mmol) of manganese(II)-carbonate. After a reaction time of 3 hours at 80° C., the now almost clear reaction solution is cooled off to room temperature and a pH of 7.2 is set with 1N sodium hydroxide solution. After filtration, the obtained filtrate is freeze-dried.

Yield: 3.43 g (97.8% of theory) of an amorphous powder Water content: 5.68% Elementary analysis (relative to anhydrous substance): Cld: C 46.92 H 5.45 N 8.42 Mn 8.26 Na 6.91 Fnd: C 46.90 H 5.42 N 8.40 Mn 8.23 Na 6.87

Example 5

3,9-Bis(tert-butoxycarbonylmethyl)-6-[2-(4-methoxyphenyl)]-carboxymethyl-3,6,9-triazaundecanedioic acid-di-tert-butyl ester a) 2-Bromo-2-(4-methoxyphenyl)-acetic acid methyl ester 27.01 g (169 mmol) of bromine is added with intensive stirring to a mixture of 18.46 g (100 mmol) of 2-(4-methoxyphenyl)-acetic acid chloride and 1.24 g (40 mmol) of red phosphorus, so that the bromine coloring fades away steadily. After about half the amount of bromine is added, it is heated for 3 more hours at 40° C. 4.49 g (140 mmol) of methanol is then instilled in the cooled solution, it is allowed to stir for one more hour, diluted with 100 ml of dichloromethane, the solution is instilled with intensive stirring in ice water, the organic phase is separated, washed with saturated sodium carbonate solution and dried on sodium sulfate and evaporated to dryness in a vacuum. The residue is purified by distillation in a bulb tube in the oil pump vacuum.

Yield: 19.59 g (75.6% of theory) Elementary analysis: Cld: C 46.36 H 4.28 Br 30.84 Fnd: C 46.42 H 4.35 Br 30.78 b) 3,9-Bis(tert-butoxycarbonylmethyl)-6-[2-(4-methoxyphenyl)]-methoxy-carbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.11 g (12 mmol) of 2-bromo-2-(4-methoxyphenylacetic acid methyl ester) are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 5.50 g (74.6% of theory) Elementary analysis: Cld: C 61.85 H 8.60 N 5.69 Fnd: C 61.78 H 8.66 N 5.75 c) 3,9-Bis(tert-butoxycarbonylmethyl)-6-[2-(4-methoxyphenyl)]-carboxymethyl-3,6,9-triazaundecanedioic acid-di-tert-butyl ester 7.38 g (10 mmol) of the compound produced under Example 5b) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained as foam.

Yield: 6.39 g (88.3% of theory) Elementary analysis: Cld: C 61.39 H 8.49 N 5.80 Fnd: C 61.31 H 8.56 N 5.74 d) 3,9-Bis(tert-butoxycarbonylmethyl)-6-[2-(4-methoxyphenyl)]-aminocarbonylmethyl-3,6,9-triazaundecanedioic acid-di-tert-butyl ester 5 g (6.91 mmol) of the title compound of Example 5c) is dissolved in 30 ml of anhydrous benzene and 1.75 g (13.82 mmol) of oxalic acid dichloride is added at 0° C. It is stirred for 3 hours at 0° C. and then evaporated to dryness in a vacuum. The residue is dissolved in 30 ml of benzene and again evaporated to dryness. At 0° C., ammonia gas is introduced into the solution with vigorous stirring (30 minutes). The solution is washed twice with 50 ml of 5% aqueous soda solution in each case, the organic phase is dried on magnesium sulfate and evaporated to dryness in a vacuum. The residue is chromatographed on silica gel (mobile solvent: methylene chloride/hexane/isopropanol =10:10:1).

Yield: 3.95 g (79% of theory) of a colorless solid Elementary analysis: Cld: C 61.47 H 8.64 N 7.75 Fnd: C 61.58 H 8.75 N 7.61 e) 3,9-Bis(carboxymethyl)-6-[2-(4-methoxyphenyl)]-aminocarbonylmethyl-3,6,9-triazaundecanedioic acid 3.5 g (4.84 mmol) of the title compound of Example 5d) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 15 ml of acid ion exchanger IR 120 (H⁺ form) is added and stirred for 10 minutes at room temperature. It is filtered off from the ion exchanger and evaporated to dryness in a vacuum.

Yield: 1.60 g (63% of theory) of a vitreous solid Water content: 5.0% Elementary analysis (relative to anhydrous substance): Cld: C 50.60 H 6.07 N 11.24 Fnd: C 50.70 H 6.15 N 11.13 f) Gadolinium complex of 3,9-bis(carboxymethyl)-6-[2-(4-methoxyphenyl)]-aminocarbonylmethyl-3,6,9-triazaundecanedioic acid-monosodium salt Analogously to Example 1i), after freeze-drying, the reaction of 2.8 g (5.61 mmol) of the title compound of Example 5e) with 1.01 g (2.80 mmol) of gadolinium oxide yields 3.74 g (99.0% of theory) of the title compound as amorphous powder.

Water content: 7.49% Elementary analysis (relative to anhydrous substance): Cld: C 37.38 H 3.88 N 8.30 Gd 23.31 Na 3.41 Fnd: C 37.31 H 3.84 N 8.28 Gd 23.28 Na 3.39 g) Manganese complex of 3,9-bis(carboxymethyl)-6-[2-(4-methoxyphenyl)]-aminocarbonylmethyl-3,6,9-triazaundecanedioic acid-disodium salt Analogously to Example 4i), after freeze-drying, the reaction of 1.8 g (3.61 mmol) of the title compound of Example 5e) with 0.41 g (3.61 mmol) of manganese(II)-carbonate yields 2.09 g (97.6% of theory) of the title compound as amorphous powder.

Water content: 4.72% Elementary analysis (relative to anhydrous substance): Cld: C 42.37 H 4.40 N 9.41 Mn 9.23 Na 7.72 Fnd: C 42.40 H 4.44 N 9.43 Mn 9.25 Na 7.74

Example 6

3,9-Bis(tert-butoxycarbonylmethyl)-6-[2-(4-ethoxybenzyl)-carboxymethyl-3,6,9-triazaundecanedioic acid-di-tert-butyl ester 2-Bromo-3-(4-ethoxyphenyl)-propionic acid ethyl ester a) 3-(4-Ethoxyphenyl)-propionic acid 16.62 g (100 mmol) of 3-(4-hydroxyphenyl)-propionic acid is dissolved with stirring and covering with argon in 45 ml (225.0 mmol) of 5N sodium hydroxide solution, and 15.73 g (100 mmol), (98%) of diethyl sulfate is instilled quickly so that the temperature does not exceed 40° C. (water cooling). After completion of the addition, it is heated for 30 more minutes to 100° C. After the cooling, it is extracted with diethyl ether, then acidified with sulfuric acid to pH 4 and the precipitated compound is taken up in ether. After drying on sodium sulfate, it is evaporated to dryness in a vacuum. The title compound is obtained as solid.

Yield: 15.21 g (78.3% of theory) Elementary analysis: Cld: C 68.02 H 7.26 Fnd: C 68.13 H 7.34 b) 2-Bromo-3-(4-ethoxyphenyl)-propionic acid ethyl ester

A drop of dimethylformamide is added to 9.71 g (50 mmol) of the acid, produced under 6a), in 50 ml of 1,2-dichloroethane. Then, it is heated to 80° C. and 5.0 ml (68.6 mmol) of thionyl chloride is instilled in it. Vigorous gas generation takes place. After completion of the addition, it is refluxed for one more hour, then evaporated to dryness in a vacuum and 0.62 g (20 mmol) of red phosphorus is added to the acid chloride. Then, 13.6 g (85 mmol) of bromine is quickly instilled with stirring so that the bromine coloring simply fades away. When about half the amount of bromine is added, it is heated to 40° C. and the temperature is maintained for three hours. It is cooled to room temperature and then 3.22 g (70 mmol) of ethanol in 20 ml of dichloromethane is instilled in it. After one hour, it is diluted with 200 ml of dichloromethane, poured on ice water, the organic solution is separated, washed with saturated sodium bicarbonate solution and evaporated to dryness in a vacuum. The title compound is purified by chromatography on silica gel. A mixture of ethyl acetate and hexane is used as eluant. The title compound is obtained as syrup.

Yield: 11.57 g (76.8% of theory) Elementary analysis: Cld: C 51.84 H 5.69 Br 26.53 Fnd: C 51.77 H 5.74 Br 26.59 c) 3,9-Bis(tert-butoxycarbonylmethyl)-6-[2-(4-ethoxybenzyl)-ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.61 g (12 mmol) of 2-bromo-2-(4-ethoxybenzyl)-acetic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.95 g (63.4% of theory) Elementary analysis: Cld: C 63.13 H 8.92 N 5.39 Fnd: C 63.07 H 8.89 N 5.44 d) 3,9-Bis(tert-butoxycarbonylmethyl)-6-[2-(4-ethoxybenzyl)-carboxymethyl-3,6,9-triazaundecanedioic acid-di-tert-butyl ester 7.80 g (10 mmol) of the compound produced under Example 6c) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained as foam.

Yield: 6.47 g (86.1% of theory) Elementary analysis: Cld: C 62.29 H 8.71 N 5.59 Fnd: C 62.36 H 8.77 N 5.57 e) 3,9-Bis(tert-butoxycarbonylmethyl)-6-[2-(4-ethoxybenzyl)]-aminocarboxymethyl-3,6,9-triazaundecanedioic acid-di-tert-butyl ester 5 g (6.65 mmol) of the title compound of Example 6d) is dissolved in 30 ml of anhydrous benzene and 1.69 g (13.30 mmol) of oxalic acid dichloride is added at 0° C. It is stirred for 3 hours at 0° C. and then evaporated to dryness in a vacuum. The residue is dissolved in 30 ml of benzene and again evaporated to dryness. At 0° C., ammonia gas in introduced in the solution with vigorous stirring (30 minutes). The solution is washed twice with 50 ml of 5% aqueous soda solution in each case, the organic phase is dried on magnesium sulfate and evaporated to dryness in a vacuum. The residue is chromatographed on silica gel (mobile solvent: methylene chloride/hexane/isopropanol= 10:10:1)

Yield: 4.05 g (81% of theory) of a colorless solid Elementary analysis: Cld: C 62.38 H 8.86 N 7.46 Fnd: C 62.45 H 8.78 N 7.35

29 f) 3,9-Bis(carboxymethyl)-6-[2-(4-ethoxybenzyl)-aminocarboxymethyl-3,6,9-triazaundecanedioic acid 4.00 g (5.32 mmol) of the title compound of Example 6e) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 15 ml of acid ion exchanger IR 120 (H⁺form) is added and stirred for 10 minutes at room temperature. It is filtered off from the ion exchanger and evaporated to dryness in a vacuum.

Yield: 1.90 g (64% of theory) of a vitreous solid Water content: 5.7% Elementary analysis (relative to anhydrous substance): Cld: C 52.47 H 6.51 N 10.64 Fnd: C 52.38 H 6.60 N 10.58

Gadolinium complex of 3,9-bis(carboxymethyl)-6-[2-(4-ethoxybenzyl)-aminocarboxymethyl-3,6,9-triazaundecanedioic acid-monosodium salt Analogously to Example 1i), after freeze-drying, the reaction of 1.9 g (3.60 mmol) of the title compound of Example 6f) with 0.65 g (1.80 mmol) of gadolinium oxide yields 2.41 g (95.5% of theory) of the title compound as amorphous powder.

Water content: 8.18% Elementary analysis (relative to anhydrous substance): Cld: C 39.31 H 4.30 N 7.97 Gd 22.98 Na 3.27 Fnd: C 39.28 H.4.26 N 7.95 Gd 22.32 Na 3.25 h) Europium complex of 3,9-bis(carboxymethyl)-6-[2-(4-ethoxybenzyl)-aminocarboxymethyl-3,6,9-triazaundecanedioic acid-monosodium salt Analogously to Example 3i), after freeze-drying, the reaction of 1.2 g (2.27 mmol) of the title compound of Example 6f) with 0.40 g (1.14 mmol) of europium oxide yields 1.52 g (96.6% of theory) of the title compound as amorphous powder.

Water content: 7.45% Elementary analysis (relative to anhydrous substance): Cld: C 39.61 H 4.34 N 8.03 Eu 21.79 Na 3.30 Fnd: C 39.62 H 4.32 N 7.99 Eu 21.78 Na 3.32

Example 7

3,9 -Bis(tert-butoxycarbonylmethyl)-6-[2-(pyrid-2-yl)]-ethoxycarbonylmethyl-3,6,9-triazaundecanedioic acid-di-tert-butyl ester a) 2-Bromo-2-(pyrid-2-yl)-acetic acid ethyl ester 16.52 g (100 mmol) of 2-pyridylacetic acid ethyl ester is dissolved in 50 ml of carbon tetrachloride. It is cooled to 0° C. and 15.98 g (100 mmol) of bromine, dissolved in 15 ml of carbon tetrachloride, is then instilled in it within 30 minutes. Then, it is allowed to react for one more hour at 25° C. The bromine coloring fades away. It is concentrated by evaporation in a vacuum and the hydrobromide of the title compound is obtained. The free compound is obtained by extraction of ether from the aqueous solution after adding sodium bicarbonate.

Yield: 22.80 g (93.4% of theory) Elementary analysis: Cld: C 44.29 H 4.13 Br 32.74 N 5.74 Fnd: C 44.22 H 4.18 Br 32.81 N 5.68 b) 3,9-Bis(tert-butoxycarbonylmethyl)-6-[2-(pyrid-2-yl)]-ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 2.93 g (12 mmol) of 2-bromo-2-(pyrid-2-yl)-acetic acid

30 ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 5.11 g (69.2% of theory) Elementary analysis: Cld: C 60.14 H 8.46 N 7.58 Fnd: C 60.21 H 8.55 N 7.66 c) 3,9-Bis(tert-butoxycarbonylmethyl)-6-[2-(pyrid-2-yl)]-carboxymethyl-3,6,9-triazaundecanedioic acid-di-tert-butyl ester 7.39 g (10 mmol) of the compound produced under Example 7b) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained as foam.

Yield: 5.96 g (87.6% of theory) Elementary analysis: Cld: C 61.74 H 6.59 N 6.17 Fnd: C 61.66 H 6.65 N 6.24 d) 3,9-Bis(tert-butoxycarbonylmethyl)-6-[2-(pyridyl-2-yl)]-(4-carboxybutyl)aminocarbonylmethyl-3,6,9-triazaundecanedioic acid-di-tert-butyl ester 5 g (7.34 mmol) of the title compound of Example 7c) and 0.74 g (7.34 mmol) of triethylamine are dissolved in 50 ml of methylene chloride. At −10° C., a solution of 1.11 g (8.1 mmol) of isobutyl chloroformate in 10 ml of methylene chloride is instilled within 5 minutes and stirred for 20 minutes at −10° C. The solution is cooled off to −15° C. and a solution of 0.86 g (7.34 mmol) of 5-aminopentanoic acid and 2.23 g (22.0 mmol) of triethylamine in 10 ml of methylene chloride is instilled within 10 minutes and stirred for 30 minutes at −15° C., then overnight at room temperature. It is extracted twice with 100 ml each of 10% aqueous ammonium chloride solution, the organic phase is dried on magnesium sulfate and evaporated to dryness in a vacuum. The residue is chromatographed on silica gel (mobile solvent: methylene chloride/ethanol=20:1).

Yield: 4.60 g (79% of theory) of a colorless solid Elementary analysis: Cld: C 60.51 H 8.50 N 8.82 Fnd: C 60.63 H 8.60 N 8.71 e) 3,9-Bis(carboxymethyl)-6-[2-(pyridyl-2-yl)]-(4-carboxybutyl)aminocarbonylmethyl-3,6,9-triazaundecanedioic acid 4.50 g (5.67 mmol) of the title compound of Example 7d) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water 20 ml of acid ion exchanger IR 120 (H⁺ form) is added and stirred for 10 minutes at room temperature. It is filtered off from the ion exchanger and evaporated to dryness in a vacuum.

Yield: 2.07 g (59% of theory) of a vitreous solid Water content: 8.1% Elementary analysis (relative to anhydrous substance): Cld: C 50.61 H 6.19 N 12.30 Fnd: C 50.50 H 6.27 N 12.36 f) Gadolinium complex of 3,9-bis(carboxymethyl)-6-[2-(pyridyl-2-yl)]-(4-carboxybutyl)aminocarbonylmethyl-3,6,9-triazaundecanedioic acid-disodium salt Analogously to Example 1i), after freeze-drying, the reaction of 2.3 g (4.04 mmol) of the title compound of Example 7e) with 0.73 g (2.02 mmol) of gadolinium oxide yields 3.05 g (98.4% of theory) of the title compound as amorphous powder.

Water content: 5.54% Elementary analysis (relative to anhydrous substance): Cld: C 37.55 H 3.94 N 9.12 Gd 20.48 Na 5.99 Fnd: C 37.51 H 3.88 N 9.10 Gd 20.46 Na 5.97 g) Iron complex of 3,9-bis(carboxymethyl)-6-[2-(pyridyl-2-yl)]-(4-carboxybutyl)aminocarbonylmethyl-3,6,9-triazaundecanedioic acid-disodium salt Analogously to Example 1j), after freeze-drying, the reaction of 1.42 g (2.49 mmol) of the title compound of Example 7e) with 0.88 g (2.49 mmol) of iron(III) acetylacetonate yields 1.59 g (96.0% of theory) of the title compound as amorphous powder.

Water content: 6.21% Elementary analysis (relative to anhydrous substance): Cld: C 43.26 H 4.54 N 10.51 Fe 8.38 Na 6.90 Fnd: C 43.25 H 4.51 N 10.48 Fe 8.36 Na 6.88

Example 8

3,9-Bis(tert-butoxycarbonylmethyl)-6-[2-(2,5-dioxahexyl)]-carboxymethyl-3,6,9-triazaundecanedioic acid-di-tert-butyl ester a) 4,7-Dioxaoctanoic acid benzyl ester 1.15 g (50.0 mmol) of sodium is dissolved in 100 ml of dried ethylene glycol monomethyl ether. Then, 5.01 g (50 mmol) of freshly distilled ethyl acrylate, dissolved in 15 ml of dry diethyl ether at 0° C., is instilled in it with stirring and exclusion of moisture. It is allowed to stir for 1 more hour at the low temperature, then 5 ml of water is added to it and heated for 2 hours to 60° C. to saponify the ester. It is concentrated by evaporation in a vacuum to 30 ml, diluted with 100 ml of water, the solution is extracted with ether and then the aqueous phase is adjusted with sulfuric acid to pH 4. The precipitated compound is taken up in diethyl ether, the solution is dried on sodium sulfate and evaporated to dryness in a vacuum. The title compound is obtained as syrup.

Yield: 6.11 g (82.5% of theory) Elementary analysis: Cld: C 48.64 H 8.16 Fnd: C 48.71 H 8.23 b) 2-Bromo-4,7-dioxaoctanoic acid benzyl ester

One drop of dimethylformamide is added to 7.41 g (50 mmol) of the acid, produced under Example 8a), in 50 ml of 1,2-dichloroethane. Then, it is heated to 80° C. and 5.0 ml (68.6 mmol) of thionyl chloride is instilled in it. Vigorous gas generation takes place. After completion of the addition, it is refluxed for one more hour and then evaporated to dryness in a vacuum. 0.62 g (20 mmol) of red phosphorus is added to the acid chloride and then 13.6 g (85 mmol) of bromine is quickly instilled with stirring so that the bromine coloring simply fades away. When about half the amount of bromine is added, it is heated to 40° C. and this temperature is maintained for three more hours. It is cooled to room temperature and the mixture of 7.57 g (70 mmol) of benzyl alcohol and 7.08 g (70 mmol) of dry triethylamine in 20 ml of dichloromethane is instilled in it. After 1 hour, it is diluted with 200 ml of dichloromethane, poured on ice water and the organic solution is separated. It is washed with saturated sodium bicarbonate solution, dried on sodium sulfate and evaporated to dryness in a vacuum. The title compound is purified by chromatography on silica gel. A mixture of ethyl acetate and hexane is used as eluant. The title compound is obtained as syrup.

Yield: 12.43 g (78.4% of theory) Elementary analysis: Cld: C 49.23 H 5.40 Br 25.19 Fnd: C 49.30 H 5.46 Br 25.10 c) 3,9-Bis(tert-butoxycarbonylmethyl)-6-[2-(2,5-dioxahexyl)]-benzyloxy-carbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.81 g (12 mmol) of 2-bromo-4,7-dioxaoctanoic acid benzyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 5.20 g (65.2% of theory) Elementary analysis: Cld: C 61.79 H 8.85 N 5.27 Fnd: C 61.87 H 8.92 N 5.22 d) 3,9-Bis(tert-butoxycarbonylmethyl)-6-[2-(2,5-dioxahexyl)]-carboxymethyl-3,6,9-triazaundecanedioic acid-di-tert-butyl ester 7.97 g (10 mmol) of the benzyl ester produced under 8c) is dissolved in 100 ml of ethanol and mixed with 0.4 g of Pearlman's catalyst (Pd 20%, C). It is hydrogenated until 224 ml of hydrogen is taken up, then suctioned off from the catalyst, washed well with ethanol and the solution is evaporated to dryness in a vacuum. The product is obtained as foam.

Yield: 6.87 g (97.3% of theory) Elementary analysis: Cld: C 57.85 H 9.00 N 5.95 Fnd: C 57.91 H 9.11 N 6.01 e) 3,9-Bis(tert-butoxycarbonylmethyl)-6-[2-(2,5-dioxahexyl)]-(2-hydroxyethyl)-aminocarbonylmethyl-3,6,9-triazaundecanedioic acid-di-tert-butyl ester 5 g (7.08 mmol) of the title compound of Example 8d) and 476 mg (7.08 mmol) of ethanolamine are dissolved in 30 ml of toluene and 1.93 g (7.79 mmol) of 2-ethoxy-1-ethoxycarbonyl-1,2-dihydroquinoline is added at 0° C. It is stirred for 30 minutes at 0° C., then overnight at room temperature. It is evaporated to dryness in a vacuum and the residue is chromatographed on silica gel (mobile solvent: hexane/ethyl acetate=15:1).

Yield: 4.93 g (93% of theory) of a colorless oil Elementary analysis: Cld: C 57.73 H 9.15 N 7.48 Fnd: C 57.61 H 9.23 N 7.35 f) 3,9-Bis(carboxymethyl)-6-[2-(2,5-dioxahexyl)]-(2-hydroxyethyl)-aminocarbonylmethyl-3,6,9-triazaundecanedioic acid 4.5 g (6.01 mmol) of the title compound of Example 8f) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 (H$^+$ form) is added and stirred for 10 minutes at room temperature. It is filtered off from the ion exchanger and evaporated to dryness in a vacuum.

Yield: 2.50 g (72% of theory) of a vitreous solid Water content: 9.1% Elementary analysis (relative to anhydrous substance): Cld: C 45.80 H 6.92 N 10.68 Fnd: C 45.93 H 6.84 N 10.75 g) Gadolinium complex of 3,9-bis(carboxymethyl)-6-[2-(2,5-dioxahexyl)]-(2-hydroxyethyl)-aminocarbonyl-methyl-3,6,9-triazaundecanedioic acid-monosodium salt Analogously to Example 1i), after freeze-drying, the reaction of 3.6 g (6.86 mmol) of the title compound of Example 8f) with 1.24 g (3.43 mmol) of gadolinium oxide yields 4.75 g (99.1% of theory) of the title compound as amorphous powder.

Water content: 6.14% Elementary analysis (relative to anhydrous substance): Cld: C 34.28 H 4.60 N 8.00 Gd 22.44 Na 3.28 Fnd: C 34.27 H 4.56 N 7.98 Gd 22.42 Na 3.26 h) Ytterbium complex of 3,9-Bis(carboxymethyl)-6-[2-(2, 5-dioxahexyl)]-(2-hydroxyethyl)aminocarbonylmethyl-3,6, 9-triazaundecanedioic acid-monosodium salt 1.6 g (3.05 mmol) of the title compound of Example 8f) is dissolved in 100 ml of deionized water and mixed at room temperature in portions with 0.60 g (1.52 mmol) of ytterbium oxide. After a reaction time of 3 hours at 80° C., the now almost clear reaction solution is cooled off to room temperature and a pH of 7.2 is set with 1N sodium hydroxide solution. After filtration, the obtained filtrated is freeze-dried.

Yield: 2.08 g (95.4% of theory) of an amorphous powder Water content: 7.66% Elementary analysis (relative to anhydrous substance): Cld: C 33.53 H 4.50 N 7.82 Yb 24.15 Na 3.21 Fnd: C 33.55 H 4.53 N 7.86 Yb 24.20 Na 3.23

Example 9

3,9-Bis(tert-butoxycarbonylmethyl)-6-(2-hydroxymethyl)-carboxymethyl-3,6,9-triazaundecanedioic acid-di-tert-butyl ester a) 3-Benzyloxy-2-bromopropionic acid methyl ester 40.3 g (339 mmol) of potassium bromide is dissolved in 200 ml of 2.5 N sulfuric acid. 19.52 g (100 mmol) of 3-benzyloxy-serine is added to it, cooled to 0° C. and 10.6 g (154 mmol) of sodium nitrite is added in the course of one hour with vigorous stirring. It is allowed to stir for one more hour at 0° C. and for another at 25° C. Then, it is extracted with ether, the solution is washed with water, dried on sodium sulfate and the carboxylic acid is esterified by adding an ethereal diazomethane solution in portions until the reaction is discernibly completed (coloring, TLC control). The solution is concentrated by evaporation in a vacuum. The title compound is purified by chromatography on silica gel with a mixture of ether and hexane as eluant. It is obtained as oil.

Yield: 22.97 g (84.1% of theory) Elementary analysis: Cld: C 48.37 H 4.80 Br 29.26 Fnd: C 48.30 H 4.86 Br 29.33 b) 3,9-Bis(tert-butoxycarbonylmethyl)-6-[2-(benzyloxymethyl)]-ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.28 g (12 mmol) of 2-bromo-3-benzyloxypropionic acid benzyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 5.09 g (67.1% of theory) Elementary analysis: Cld: C 63.39 H 7.85 N 5.54 Fnd: C 63.51 H 7.90 N 5.59 c) 3,9-Bis(tert-butoxycarbonylmethyl)-6-(2-hydroxymethyl)-carboxymethyl-3,6,9-triazaundecanedioic acid-di-tert-butyl ester 7.52 g (10 mmol) of the benzyl ether produced under 9b) is dissolved in 100 ml of ethanol and mixed with 0.4 g of Pearlman's catalyst (Pd 20%, C). It is hydrogenated until 224 ml of hydrogen is taken up, then suctioned off from the catalyst, rewashed well with ethanol and evaporated to dryness in a vacuum. The product is obtained as foam.

Yield: 5.71 g (88.1% of theory) Elementary analysis: Cld: C 57.48 H 8.87 N 6.49 Fnd: C 57.60 H 8.98 N 6.59 d) 3,9-Bis(tert-butoxycarbonylmethyl)-6-(2-hydroxymethyl)-(2,2-dimethyl-6-hydroxy-1,3-dioxepan-5-yl)-aminocarbonylmethyl-3,6,9-triazaundecanedioic acid-di-tert-butyl ester 5 g (7.72 mmol) of the title compound of Example 9c) and 781 mg (7.72 mmol) of triethylamine are dissolved in 50 ml of methylene chloride. At −10° C., a solution of 1.16 g (8.5 mmol) of isobutyl chloroformate in 10 ml of methylene chloride is instilled within 5 minutes and stirred for 20 minutes at −10° C. The solution is cooled off to −15° C. and a solution of 1.24 g (7.72 mmol) of 5-amino-2,2-dimethyl-1,3-dioxepan-6-ol and 2.12 g (21 mmol) of triethylamine in 10 ml of methylene chloride is instilled within 10 minutes and stirred for 30 minutes at −15° C., then overnight at room temperature. It is extracted twice with 100 ml each of 10% aqueous ammonium chloride solution, the organic phase is dried on magnesium sulfate and evaporated to dryness in a vacuum. The residue is chromatographed on silica gel (mobile solvent: methylene chloride/ethanol =20:1).

Yield: 4.50 g (79% of theory) of a colorless solid Elementary analysis: Cld: C 57.70 H 8.92 N 7.08 Fnd: C 57.60 H 9.05 N 7.15 e) 3,9-Bis(carbonylmethyl)-6-(2-hydroxymethyl)-[1-(hydroxymethyl)-2,3-dihydroxypropyl]-aminocarbonylmethyl-3,6,9-triazaundecanedioic acid 4 g (5.06 mmol) of the title compound of Example 9d) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 (H$^+$ form) is added and stirred for 10 minutes at room temperature. It is filtered off from the ion exchanger and evaporated to dryness in a vacuum.

Yield: 1.76 g (61% of theory) of a vitreous solid Water content: 7.5% Elementary analysis (relative to anhydrous substance): Cld: C 43.34 H 6.51 N 10.64 Fnd: C 43.25 H 6.65 N 10.51 f) Gadolinium complex of 3,9-bis(carbonylmethyl)-6-(2-hydroxymethyl)-[1-(hydroxymethyl)-2,3-dihydroxypropyl]-aminocarbonylmethyl-3,6,9-triazaundecanedioic acid-monosodium salt Analogously to Example 1i), after freeze-drying, the reaction of 4.10 g (7.78 mmol) of the title compound of Example 9e) with 1.41 g (3.89 mmol) of gadolinium oxide yields 5.18 g (94.8% of theory) of the title compound as amorphous powder.

Water content: 9.53% Elementary analysis (relative to anhydrous substance): Cld: C 32.48 H 4.30 N 7.97 Gd 22.38 Na 3.27 Fnd: C 32.51 H 4.32 N 7.99 Gd 22.42 Na 3.30 g) Manganese complex of,3,9-bis(carbonylmethyl)-6-(2-hydroxymethyl)-[1-(hydroxymethyl)-2,3-dihydroxypropyl]-aminocarbonylmethyl-3,6,9-triazaundecanedioic acid-disodium salt Analogously to Example 4i), after freeze-drying, the reaction of 3.30 g (6.26 mmol) of the title compound of Example 9e) with 0.72 g (6.26 mmol) of manganese(II) carbonate yields 3.71 g (95.3% of theory) of the title compound as amorphous powder.

Water content: 8.83% Elementary analysis (relative to anhydrous substance): Cld: C 36.61 H 4.85 N 8.99 Mn 8.81 Na 7.38 Fnd: C 36.58 H 4.82 N 8.96 Mn 8.79 Na 7.36

Example 10

3,9-Bis(tert-butoxycarbonylmethyl)-6-[2-(4-benzyloxycarbonylamino)-butyl]-carboxymethyl-3, 6,9-triazaundecanedioic acid-di-tert-butyl ester a) 3,9-Bis(tert-butoxycarbonylmethyl)-6-[2-(4-bromo)-butyl]-ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.62 g (12 mmol) of 2,6-dibromohexanoic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/ hexane is used as eluant.

Yield: 4.90 g (62.7% of theory) Elementary analysis: Cld: C 55.38 H 8.52 Br 10.23 N 5.38 Fnd: C 55.48 H 8.59 Br 10.34 N 5.31 b) 3,9-Bis(tert-butoxycarbonylmethyl)-6-[2-(4-benzyloxycarbonylamino)-butyl]-carboxymethyl-3,6,9-triazaundecanedioic acid-di-tert-butyl ester 7.81 g (10 mmol) of the compound produced under Example 10a) is dissolved in 50 ml of nitromethane and mixed with 1.56 (10.4 mmol) of silver cyanate. It is stirred with exclusion of moisture for 70 hours at room temperature. Then, it is mixed with 1.62 g (15 mmol) of benzyl alcohol and allowed to stir for another 3 hours at room temperature. Then, it is diluted with 200 ml of diethyl ether, filtered off from silver salt, the solution is concentrated by evaporation in a vacuum and the residue is purified by column chromatography on silica gel. A mixture of ethyl acetate and hexane is used as eluant. The title compound is obtained as amorphous foam.

Yield: 5.84 g (68.6% of theory) Elementary analysis: Cld: C 62.10 H 8.76 N 6.58 Fnd: C 62.23 H 8.83 N 6.67 c) 3,9-Bis(tert-butoxycarbonylmethyl)-6-[2-(4-benzyloxycarbonylamino)-butyl]-aminocarbonylmethyl-3, 6,9-triazaundecanedioic acid-di-tert-butyl ester 5 g (6.65 mmol) of the title compound of Example 10b) is dissolved in 30 ml of anhydrous benzene and 1.54 g (12.15 mmol) of oxalic acid dichloride is added at 0° C. It is stirred for 3 hours at 0° C. and then evaporated to dryness in a vacuum. The residue is dissolved in 30 ml of benzene and again evaporated to dryness. At 0° C., ammonia gas is introduced into the solution with vigorous stirring (30 minutes). The solution is washed twice with 50 ml of 5% aqueous soda solution in each case, the organic phase is dried on magnesium sulfate and evaporated to dryness in a vacuum. The residue is chromatographed on silica gel (mobile solvent: methylene chloride/hexane/isopropanol =10:10:1)

Yield: 4.2 g (84% of theory) of a colorless solid Elementary analysis: Cld: C 61.37 H 8.71 N 8.52 Fnd: C 61.25 H 8.80 N 8.43 d) 3,9-Bis(tert-butoxycarbonylmethyl)-6-[2-(4-amino)-butyl]-aminocarbonylmethyl-3,6,9-triazaundecanedioic acid-di-tert-butyl ester 4.0 g (4.87 mmol) of the title compound of Example 10c) is dissolved in 100 ml of isopropanol, and 2 g of palladium catalyst (10% Pd on carbon) is added. It is hydrogenated overnight at room temperature. It is filtered off from the catalyst and the filtrate is evaporated to dryness in a vacuum. The residue is chromatographed on silica gel (mobile solvent: methylene chloride/ethanol=25:1).

Yield: 3.05 g (91% of theory) of a colorless oil Elementary analysis: Cld: C 59.36 H 9.52 N 10.18 Fnd: C 59.27 H 9.61 N 10.27 e) 3,9-Bis(carboxymethyl)-6-[2-(4-amino)-butyl]-aminocarbonylmethyl-3,6,9-triazaundecanedioic acid 3.0 g (4.36 mmol) of the title compound of Example 10d) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 ($H^+$form) is added and stirred for 10 minutes at room temperature. It is filtered off from the ion exchanger and evaporated to dryness in a vacuum.

Yield: 1.23 g (57% of theory) of a vitreous solid Water content: 6.7% Elementary analysis (relative to anhydrous substance): Cld: C 46.64 H 7.18 N 15.11 Fnd: C 46.60 H 7.09 N 15.00 f) Gadolinium complex of 3,9-bis(carboxymethyl)-6-[2-(4-amino)-butyl]-aminocarbonylmethyl-3,6,9-triazaundecanedioic acid-monosodium salt Analogously to Example 1i), after freeze-drying, the reaction of 2.7 g (5.82 mmol) of the title compound of Example 10e) with 1.05 g (2.91 mmol) of gadolinium oxide yields 3.54 g (95.3% of theory) of the title compound as amorphous powder.

Water content: 6.48% Elementary analysis (relative to anhydrous substance): Cld: C 33.80 H 4.57 Gd 24.58 N 10.95 Na 3.59 Fnd: C 33.78 H 4.55 Gd 24.52 N 10.93. Na 3.56 g) Iron complex of 3,9-bis(tert-butoxycarbonylmethyl)-6-[2-(4-benzyloxycarbonylamino)-butyl]-aminocarbonylmethyl-3,6,9-triazaundecanedioic acid-di-tert-butyl ester-monosodium salt Analogously to Example 1j), after freeze-drying, the reaction of 1.5 g (3.23 mmol) of the title compound of Example 10e) with 1.14 g (3.23 mmol) of iron(II) acetylacetonate yields 1.70 g (98.4% of theory) of the title compound as amorphous powder.

Water content: 7.31% Elementary analysis (relative to anhydrous substance): Cld: C 40.16 H 5.43 N 13.01 Fe 10.37 Na 4.27 Fnd: C 40.10 H 5.39 N 12.98 Fe 10.35 Na 4.25

Example 11

3,9-Bis(tert-butoxycarbonylmethyl)-6-carboxymethyl-3,6,9-triazaundecanedioic acid-di-tert-butyl ester a) 3,9-Bis(tert-butoxycarbonylmethyl)-6-benzyloxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 2.58 g (12 mmol) of 2-bromoacetic acid benzyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/ hexane is used as eluant.

Yield: 6.32 g (89.3% of theory) Elementary analysis: Cld: C 64.65 H 9.00 N 5.95 Fnd: C 64.62 H 9.07 N 5.90 b) 3,9-Bis(tert-butoxycarbonylmethyl)-6-carboxymethyl-3,6,9-triazaundecanedioic acid-di-tert-butyl ester 7.08 g (10 mmol) of the benzyl ester produced under 11a) is dissolved in 100 ml of ethanol and mixed with g of Pearlman's catalyst (Pd 20%, C). It is hydrogenated until 224 ml of hydrogen is taken up, suctioned off from the catalyst, rewashed well with ethanol and the solution is evaporated to dryness in a vacuum. The product is obtained as foam, which crystallized from ether/hexane.

Yield: 6.87 g (97.3% of theory) Melting point: 73°–75° C. Elementary analysis: Cld: C 57.85 H 9.00 N 5.95 Fnd: C 57.91 H 9.11 N 6.01 c) 3,9-Bis(tert-butoxycarbonylmethyl)-6-(2-aminoethyl)-aminocarbonylmethyl-3,6,9-triazaundecanedioic acid-di-tert-butyl ester 5.00 g (8.09 mmol) of the title compound of Example 11b) is dissolved in 25 ml of dimethylformamide, and 1.02 g (8.90 mol) of N-hydroxysuccinimide is added. It is cooled off to 0° C. and 1.84 g (8.90 mmol) of dicyclohexylcarbodiimide is added. It is stirred for 1 hour at 0° C. and then stirred for 4 hours at room temperature. It is cooled off to 0° C. and a solution of 2.67 g of 1.2 diaminoethane (44.5 mmol) in 50 ml of dimethylformamide is instilled within 10 minutes. It is stirred for one hour at 0° C., then overnight at room temperature. It is evaporated to dryness in a vacuum, and the residue is taken up in 100 ml of ethyl acetate. It is filtered off from precipitated urea and the filtrate is washed twice with 100 ml each of 5% aqueous soda solution. The organic phase is dried on magnesium sulfate and evaporated to dryness in a vacuum. The residue is chromatographed on silica gel (mobile solvent: n-hexane/isopropanol 15:1). 2.83 g (53% of theory) of a colorless oil is obtained.

Elementary analysis: Cld: C 58.25 H 9.32 N 10.61 Fnd: C 58.17 H 9.25 N 10.55 d) 3,9-Bis(carboxymethyl)-6-(2-aminoethyl) aminocarbonylmethyl-3,6,9-triazaundecanedioic acid 2.60 g (3.94 mmol) of the title compound of Example 11c) is dissolved in 100 ml of trifluoroacetic acid. It is stirred overnight at room temperature. It is evaporated to dryness in a vacuum, and the residue is chromatographed on silica gel (mobile solvent: ethanol/25% ammonia water 20:1). The fractions containing the product are evaporated to dryness in a vacuum. The residue is dissolved in 100 ml of water. 15 ml of acid ion exchanger IR 120 ($H^+$ form) is added and stirred for 10 minutes at room temperature. It is filtered from the ion exchanger and evaporated to dryness in a vacuum.

Yield: 1.29 g (57% of theory) of a vitreous solid Water content: 7.9% Elementary analysis (relative to anhydrous substance): Cld: C 44.13 H 6.71 N 16.08 Fnd: C 40.25 H 6.63 N 16.18 e) Gadolinium complex of 3,9-bis(carboxymethyl)-6-(2-aminoethyl)-aminocarbonylmethyl-3,6,9-triazaundecanedioic acid-monosodium salt Analogously to Example 1i), after freeze-drying, the reaction of 1.20 g (2.75 mmol) of the title compound of Example 11d) with 0.50 g (1.37 mmol) of gadolinium oxide yields 1.64 g (97.8% of theory) of the title compound as amorphous powder.

Water content: 7.93% Elementary analysis (relative to anhydrous substance): Cld: C 31.42 H 4.12 Gd 25.71 N 11.45 Na 3.76 Fnd: C 31.46 H 4.14 Gd 25.74 N 11.48 Na 3.80 f) Ytterbium complex of 3,9-bis(carboxymethyl)-6-(2-aminoethyl)-aminocarbonylmethyl-3,6,9-triazaundecanedioic acid-monosodium salt Analogously to Example 8h), after freeze-drying, the reaction of 1.0 g (2.29 mmol) of the title compound of Example 11d) with 0.45 g (1.15 mmol) of ytterbium oxide yields 1.40 g (97.5% of theory) of the title compound as amorphous powder.

Water content: 8.06% Elementary analysis (relative to anhydrous substance): Cld: C 30.63 H 4.02 N 11.16 Na 3.66 Yb 27.58 Fnd: C 30.59 H 4.00 N 11.13 Na 3.61 Yb 27.51 g) Europium complex of 3,9-bis(carboxymethyl)-6-(2-aminoethyl)-aminocarbonylmethyl-3,6,9-triazaundecanedioic acid-monosodium salt Analogously to Example 3i), after freeze-drying, the reaction of 1.0 g (2.29 mmol) of the title compound of Example 11d) with 0.40 g (1.15 mmol) of europium oxide yields 1.36 g (98.0% of theory) of the title compound as amorphous powder.

Water content: 8.02% Elementary analysis (relative to anhydrous substance): Cld: C 31.69 H 4.16 N 11.55 Eu 25.06 Na 3.79 Fnd: C 31.66 H 4.10 N 11.51 Eu 25.01 Na 3.72

Example 12 a) 3,9-Bis(tert-butoxycarbonylmethyl)-6-(3-oxa-5-aminopentyl)-aminocarbonylmethyl-3,6,9-triazaundecanedioic acid-di-tert-butyl ester 5.00 g (8.09 mmol) of the title compound of Example 11b) is dissolved in 25 ml of dimethylformamide, and 1.02 g (8.90 mol) of N-hydroxysuccinimide is added. It is cooled off to 0° C. and 1.84 g (8.90 mmol) of dicyclohexylcarbodiimide is added. It is stirred for 1 hour at 0° C. and then stirred for 4 hours at room temperature. It is cooled off to 0° C. and a solution of 2.67 g of 1.5 diamino-3-oxa-pentane (44.5 mmol) in 50 ml of dimethylformamide is instilled within 10 minutes. It is stirred for one hour at 0° C., then overnight at room temperature. It is evaporated to dryness in a vacuum, and the residue is taken up in 100 ml of ethyl acetate. It is filtered off from precipitated urea and the filtrate is washed twice with 100 ml each of 5% aqueous soda solution. The organic phase is dried on magnesium sulfate and evaporated to dryness in a vacuum. The residue is chromatographed on silica gel (mobile solvent: n-hexane/ ethyl acetate 20:1). 2.79 g (49% of theory) of a colorless oil is obtained.

Elementary analysis: Cld: C 58.01 H 9.31 N 9.95 Fnd: C 57.90 H 9.41 N 9.87 b) 3,9-Bis(carboxymethyl)-6-(3-oxa-5-aminopentyl) aminocarbonylmethyl-3,6,9-triazaundecanedioic acid 2.60 g (3.69 mmol) of the title compound of Example 1g) is dissolved in 100 ml of trifluoroacetic acid. It is stirred overnight at room temperature. It is evaporated to dryness in a vacuum, and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 ($H^+$form) is added and stirred for 10 minutes at room temperature. It is filtered off from the ion exchanger and evaporated to dryness in a vacuum.

Yield: 1.11 g (57% of theory) of a vitreous solid Water content: 8.9% Elementary analysis: Cld: C 45.09 H 6.94 N 14.61 Fnd: C 45.17 H 6.86 N 14.55 c) Gadolinium complex of 3,9-bis(carboxymethyl)-6-(3-oxa-5-aminopentyl)-aminocarbonylmethyl-3,6,9-triazaundecanedioic acid-monosodium salt Analogously to Example 1i), after freeze-drying, the reaction of 2.4 g (5.00 mmol) of the title compound of Example 12b) with 0.90 g (2.50 mmol) of gadolinium oxide yields 3.23 g (98.6% of theory) of the title compound as amorphous powder.

Water content: 6.47% Elementary analysis (relative to anhydrous substance): Cld: C 32.97 H 4.46 N 10.68 Gd 23.98 Na 3.51 Fnd: C 32.91 H 4.44 N 10.63 Gd 23.92 Na 3.48 d) Dysprosium complex of 3,9-bis(carboxymethyl)-6-(3-oxa-5-aminopentyl)-aminocarbonylmethyl-3,6,9-triazaundecanedioic acid-monosodium salt Analogously to Example 2j), after freeze-drying, the reaction of 1.8 g (3.75 mmol) of the title compound of Example 12b) with 0.70 g (1.87 mmol) of dysprosium oxide yields 2.40 g (96.8% of theory) of the title compound as amorphous powder.

Water content: 7.13% Elementary analysis (relative to anhydrous substance): Cld: C 32.71 H 4.42 N 10.60 Dy 24.59 Na 3.48 Fnd: C 32.68 H 4.39 N 10.57 Dy 24.55 Na 3.41

Example 13 a) 3,9-Bis(tert-butoxycarbonylmethyl)-6-bis(octadecyl)-aminocarbonylmethyl-3,6,9-triazaundecanedioic acid-di-tert-butyl ester 5 g (8.09 mmol) of the title compound of Example 11b) and 4.22 g (8.09 mmol) of bis-octadecylamine are dissolved in 30 ml of toluene, and 2.20 g (8.9 mmol) of 2-ethoxy-1-ethoxycarbonyl-1,2-dihydroquinoline is added at 0° C. It is stirred for 30 minutes at 0° C., then overnight at room temperature. It is evaporated to dryness in a vacuum and the residue is chromatographed on silica gel (mobile solvent: hexane/ethyl acetate 20:10:1).

Yield: 7.99 g (88% of theory) of a colorless solid Elementary analysis: Cld: C 70.67 H 11.50 N 4.99 Fnd: C 70.78 H 11.60 N 4.83 b) 3,9-Bis(carboxymethyl)-6-bis(octadecyl)aminocarbonylmethyl-3,6,9-triazaundecanedioic acid 5 g (4.46 mmol) of the title compound of Example 13a) is dissolved in 100 ml of trifluoroacetic acid and stirred overnight at room temperature. It is evaporated to dryness in a vacuum and the residue is chromatographed on silica gel (mobile solvent: methylene chloride/ethanol/33% ammonia water 20:5:0.5). The fractions containing the product are evaporated to dryness in a vacuum and the residue is dissolved in a mixture of 80 ml of ethanol/20 ml of water/30 ml of chloroform. 20 ml of acid ion exchanger IR 120 (H$^+$ form) is added and stirred for 30 minutes. It is filtered off from the ion exchanger and the filtrate is evaporated to dryness in a vacuum.

Yield: 2.67 g (65% of theory) of a glass-like solid Water content: 2.7% Elementary analysis: Cld: C 67.11 H 10.90 N 7.57 Fnd: C 67.21 H 10.98 N 7.46 c) Gadolinium complex of 3,9-bis(carboxymethyl)-6-bis(octadecyl)-amino-carbonylmethyl-3,6,9-triazaundecanedioic acid-monosodium salt 2.0 g (2.22 mmol) of the title compound of Example 13b) is dissolved in 100 ml of water/ethanol/chloroform (2:1:1)-mixture in boiling heat and mixed at 80° C. in portions with 0.40 g (1.11 mmol) of gadolinium oxide. Then, the thus obtained reaction solution is refluxed for 5 hours. After cooling off to room temperature, the solvent mixture is completely drawn off in a vacuum and the remaining residue is mixed with 200.ml of a water/n-butanol mixture (1:1). With vigorous stirring, pH 7.2 is set by mixing with 1 N sodium hydroxide solution. After the separation of the butanol phase, the remaining aqueous phase is extracted completely with n-butanol. Then, the combined organic phases are evaporated dryness in a vacuum.

Yield: 1.96 g (82.4% of theory) of a glass-like solid Water content: 6.16% Elementary analysis (relative to anhydrous substance): Cld: C 55.94 H 8.64 Gd 14.65 N 5.22 Na 2.14 Fnd: C 55.90 H 8.59 Gd 14.62 N 5.18 Na 2.11 d) iron complex of 3,9-bis(carboxymethyl)-6-bis(octadecyl)-aminocarbonylmethyl-3,6,9-triazaundecanedioic acid-monosodium salt 1.0 g (1.11 mmol) of the title compound of Example 13b) is dissolved in 75 ml of water/ethanol/chloroform (2:1:1)-mixture in boiling heat and mixed at 80° C. in portions with 0.39 g (1.11 mmol) of iron(III)acetylacetonate. Then, the thus obtained reaction solution is refluxed for 5 hours. After cooling off to room temperature, the solvent mixture is completely drawn off in a vacuum, and the remaining residue is mixed with 150 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined organic phases are evaporated to dryness in a vacuum.

Yield: 0.87 g (81.0% of theory) of a glass-like solid Water content: 5.93% Elementary analysis (relative to anhydrous substance): Cld: C 61.78 H 9.54 N 5.76 Fe 5.74 Na 2.36 Fnd: C 61.82 H 9.57 N 5.81 Fe 5.76 Na 2.41 e) Dysprosium complex of 3,9-bis(carboxymethyl)-6-bis(octadecyl)-aminocarbonylmethyl-3,6,9-triazaundecanedioic acid-monosodium salt 1.25 g (1.39 mmol) of the title compound of Example 13b) is dissolved in 75 ml of water/ethanol/chloroform (2:1:1)-mixture in boiling heat and mixed at 80° C. in portions with 0.26 g (0.69 mmol) of dysprosium oxide. Then, the thus obtained reaction solution is refluxed for 5 hours. After cooling off to room temperature, the solvent mixture is completely drawn off in a vacuum and the remaining residue is mixed with 150 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined organic phases are evaporated to dryness in a vacuum.

Yield: 1.34 g (89.6% of theory) of a glass-like solid Water content: 5.85% Elementary analysis (relative to anhydrous substance): Cld: C 55.67 H 8.60 Dy 15.06 N 5.19 Na 2.13 Fnd: C 55.61 H 8.76 Dy 15.02 N 5.16 Na 2.10 f) Manganese complex of 3,9-bis(carboxymethyl)-6-bis(octadecyl)-aminocarbonylmethyl-3,6,9-triazaundecanedioic acid-disodium salt 2.0 g (2.22 mmol) of the title compound of Example 13b) is dissolved in 150 ml of water/ethanol/chloroform (2:1:1)-mixture in boiling heat and mixed at 80° C. in portions with 0.25 g (2.22 mmol) of manganese(II)carbonate. Then, the thus obtained reaction solution is refluxed for 5 hours. After cooling off to room temperature, the solvent mixture is completely drawn off in a vacuum and the remaining residue is mixed with 200 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined organic phases are evaporated to dryness in a vacuum.

Yield: 1.86 g (84.2% of theory) of a glass-like solid Water content: 5.79% Elementary analysis (relative to anhydrous substance): Cld: C 60.40 H 9.33 Mn 5.53 N 5.64 Na 4.62 Fnd: C 60.33 H 9.29 Mn 5.51 N 5.60 Na 4.59

Example 14 a) Bis(octadecyl)-aminoacetic acid 30 g (57.47 mmol) of bis-octadecylamine and 8.38 g (60.3 mmol) of bromoacetic acid are dissolved in a mixture of 150 ml of toluene/10 ml of dioxane and refluxed overnight. 200 ml of 5% ammonia water is added and stirred for 10 minutes. The organic phase is separated, dried on magnesium sulfate and evaporated to dryness in a vacuum. The residue is chromatographed on silica gel (mobile solvent: methylene chloride/ethanol=20:1).

Yield: 20.33 g (61% of theory) of a waxy solid Elementary analysis: Cld: C 78.69 H 13.38 N 2.41 Fnd: C 78.80 H 13.50 N 2.34 b) 1-[Bis(octadecyl)amino]-2-oxo-3-aza-13-aminotridecane 10 g (17.24 mmol) of the title compound of Example 14a) and 2.18 g (18.96 mmol) of N-hydroxysuccinimide are dissolved in 100 ml of dimethylformamide. It is cooled to 0° C. and 3.91 g (18.96 mmol) of dicyclohexylcarbodiimide is added. It is stirred for 1 hour at 0° C., then for 3 hours at room temperature. It is filtered off from precipitated urea and the filtrate is instilled within 30 minutes in a solution of 9.80 g (56.88 mmol) of diaminodecane and 5.76 g (56.88 mmol) of triethylamine in 200 ml of methylene chloride. It is stirred overnight at room temperature. It is evaporated to dryness in a vacuum, and the residue is dissolved in 200 ml of toluene. The organic phase is washed twice with 100 ml each of 5% aqueous soda solution, dried on magnesium sulfate and evaporated to dryness in a vacuum. The residue is chromatographed on silica gel (mobile solvent: methylene chloride/isopropanol/triethylamine=50:2:1).

Yield: 5.19 g (41% of theory) of a waxy solid Elementary analysis: Cld: C 78.51 H 13.59 N 5.72 Fnd: C 78.61 H 13.68 N 5.60 c) 3,9-Bis(tert-butoxycarbonylmethyl)-6-[11-aza-13-bis(octadecyl)amino-12-oxo-tridecyl]aminocarbonylmethyl-3,6,9-triazaundecanedioic acid-di-tert-butyl ester 5 g (8.09 mmol) of the title compound of Example 11b) is dissolved in 25 ml of dimethylformamide, and 1.44 g (8.9 mmol) of N,N'-carbonyldiimidazole is added. It is stirred for 4 hours at room temperature. The solution is cooled off to 0° C., and a solution of 5.94 g (8.09 mmol) of the title compound of Example 14b) and 0.82 g (8.09 mmol) of triethylamine, dissolved in 50 ml of methylene chloride, is instilled within 30 minutes. It is stirred overnight at room temperature. It is evaporated to dryness, the residue is taken up in 150 mol of toluene and extracted twice with 100 ml each of 5% aqueous soda solution. The organic phase is dried on magnesium sulfate and concentrated by evaporation in a vacuum. The residue is chromatographed on silica gel (mobile solvent: methylene chloride/hexane/acetone= 20:10:1).

Yield: 8.42 g (78% of theory) of a waxy solid Elementary analysis: Cld: C 70.22 H 11.48 N 6.30 Fnd: C 70.31 H 11.59 N 6.17 d) 3,9-Bis(carboxymethyl)-6-[11-aza-13-bis(octadecyl) amino-12-oxo-tridecyl]aminocarbonylmethyl-3,6,9-triazaundecanedioic acid 5 g (3.75 mmol) of the title compound of Example 14c) is dissolved in 100 ml of trifluoroacetic acid and stirred overnight at room temperature. It is evaporated to dryness in a vacuum, and the residue is chromatographed on silica gel (mobile solvent: methylene chloride/ethanol/33% ammonia water 20:5:0.5). The fractions containing the product are evaporated to dryness in a vacuum and the residue is dissolved in a mixture of 80 ml of ethanol/20 ml of water/30 ml of chloroform. 15 ml of acid ion exchanger IR 120 (H$^+$ form) is added and stirred for 30 minutes. It is filtered off from the ion exchanger and the filtrate is evaporated to dryness in a vacuum.

Yield: 3.05 g (71% of theory) of a glass-like solid Water content: 3.1% Elementary analysis: Cld: C 67.11 H 10.90 N 7.57 Fnd: C 67.21 H 10.98 N 7.46 e) Gadolinium complex of 3,9-bis(carboxymethyl)-6-[11-aza-13-bis(octadecyl)amino-12-oxo-tridecyl] aminocarbonylmethyl-3,6,9-triazaundecanedioic acid-monosodium salt 2.5 g (2.25 mmol) of the title compound of Example 14d) is dissolved in 150 ml of water/ethanol/chloroform (2:1:1) -mixture in boiling heat and mixed at 80° C. in portions with 0.40 g (1.12 mmol) of gadolinium oxide. Then, the thus obtained reaction solution is refluxed for 5 hours. After cooling off to room temperature, the solvent mixture is completely drawn off in a vacuum and the remaining residue is mixed with 250 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined organic phases are evaporated to dryness in a vacuum.

Yield: 2.67 g (92.4% of theory) of a glass-like solid Water content: 6.31% Elementary analysis (relative to anhydrous substance): Cld: C 57.91 H 9.09 Gd 12.23 N 6.54 Na 1.79 Fnd: C 57.87 H 9.02 Gd 12.20 N 6.52 Na 1.77 f) Manganese complex of 3,9-bis(carboxymethyl)-6-[11-aza-13-bis(octadecyl)amino-12-oxo-tridecyl]aminocarbonylmethyl-3,6,9-triazaundecanedioic acid-disodium salt 1.5 g (1.35 mmol) of the title compound of Example 14d) is dissolved in 100 ml of water/ethanol/chloroform (2:1:1) -mixture in boiling heat and mixed at 80° C. in portions with 0.15 g (1.35 mmol) of manganese(II)carbonate. Then, the thus obtained reaction solution is refluxed for 5 hours. After cooling off to room temperature, the solvent mixture is completely drawn off in a vacuum and the remaining residue is mixed with 150 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined organic phases are evaporated to dryness in a vacuum.

Yield: 1.38 g (85.1% of theory) of a glass-like solid Water content: 7.02% Elementary analysis (relative to anhydrous substance): Cld: C 61.72 H 9.69 N 6.97 Mn 4.55 Na 3.81 Fnd: C 61.68 H 9.67 N 6.94 Mn 4.50 Na 3.78

Example 15 a) 3,9-Bis(tert-butoxycarbonylmethyl)-6-[3-aza-4-oxoheneicosyl)-aminocarbonylmethyl-3,6,9-triazaundecanedioic acid-di-tert-butyl ester 5 g (7.58 mmol) of the title compound of Example 11c) and 2.30 g (22.73 mmol) of triethylamine are dissolved in 40 ml of methylene chloride. At 0° C., a solution of 2.53 g (8.34 mmol) of octadecanoic acid chloride in 20 ml of methylene chloride is instilled within 20 minutes. It is stirred overnight at room temperature. It is extracted with 50 ml of 5% aqueous salt solution, the organic phase is dried on magnesium sulfate and evaporated to dryness. The residue is chromatographed on silica gel (mobile solvent: methylene chloride/hexane/isopropanol =20:10:1).

Yield: 6.39 g (91% of theory) of a waxy solid Elementary analysis: Cld: C 64.83 H 10.34 N 7.56 Fnd: C 64.73 H 10.40 N 7.48 b) 3,9-Bis(carboxymethyl)-6-[3-aza-4-oxo-heneicosyl)-aminocarbonylmethyl-3,6,9-triazaundecanedioic acid 5 g (5.4 mmol) of the title compound of Example 15a) is dissolved in 100 ml of trifluoroacetic acid and stirred overnight at room temperature. It is evaporated to dryness in a vacuum, and the residue is chromatographed on silica gel (mobile solvent: methylene chloride/ethanol/33% ammonia water 20:5:0.5). The fractions containing the product are evaporated to dryness in a vacuum, and the residue is dissolved in a mixture of 80 ml of ethanol/20 ml of water/30 ml of chloroform. 15 ml of acid ion exchanger IR 120 ($H^+$ form) is added and stirred for 30 minutes. It is filtered off from the ion exchanger, and the filtrate is evaporated to dryness in a vacuum.

Yield: 2.51 g (64% of theory) of a glass-like solid Water content: 3.5% Elementary analysis (relative to anhydrous substance): Cld: C 58.18 H 9.05 N 9.98 Fnd: C 58.03 H 9.14 N 9.89 c) Gadolinium complex of 3,9-bis(carboxymethyl)-6-[3-aza-4-oxo-heneicosyl)-aminocarbonylmethyl-3,6,9-triazaundecanedioic acid-monosodium salt 2.0 g (2.85 mmol) of the title compound of Example 15b) is dissolved in 150 ml of water/ethanol/chloroform (2:1:1) -mixture in boiling heat and mixed at 80° C. in portions with 0.51 g (1.42 mmol) of gadolinium oxide. Then, the thus obtained reaction solution is refluxed for 5 hours. After cooling off to room temperature, the solvent mixture is completely drawn off in a vacuum, and the remaining residue is mixed with 250 ml of a water/n-butanol mixture (1:1). With vigorous stirring, pH 7.2 is set by mixing with 1 N sodium hydroxide solution. After the separation of the butanol phase, the remaining aqueous phase is extracted completely with n-butanol. Then, the combined organic phases are evaporated to dryness in a vacuum.

Yield: 2.06 g (82.6% of theory) of a glass-like solid Water content: 7.66% Elementary analysis (relative to anhydrous substance): Cld: C 46.51 H 6.77 Gd 17.91 N 7.98 Na 2.62 Fnd: C 46.48 H 6.73 Gd 17.88 N 7.95 Na 2.59 d) Manganese complex of 3,9-bis(carboxymethyl)-6-[3-aza-4-oxo-heneicosyl)-aminocarbonylmethyl-3,6,9-triazaundecanedioic acid-disodium salt 1.5 g (2.13 mmol) of the title compound of Example 15b) is dissolved in 100 ml of water/ethanol/chloroform (2:1:1)-mixture in boiling heat and mixed at 80° C. in portions with 0.24 g (2.13 mmol) of manganese(II)carbonate. Then, the thus obtained reaction solution is refluxed for 5 hours. After cooling off to room temperature, the solvent mixture is completely drawn off in a vacuum, and the remaining residue is mixed with 200 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined organic phases are evaporated to dryness in a vacuum.

Yield: 1.50 g (88.6% of theory) of a glass-like solid Water content: 6.41% Elementary analysis: Cld: C 51.12 H 7.45 Mn 6.88 N 8.77 Na 5.76 Fnd: C 51.08 H 7.40 Mn 6.84 N 8.74 Na 5.73

Example 16 a) 3,9-Bis(tert-butoxycarbonylmethyl)-6-(10-carboxydecyl)-aminocarbonylmethyl-3,6,9-triazaundecanedioic acid-di-tert-butyl ester 5 g (8.09 mmol) of the title compound of Example 11b) and 0.82 g (8.09 mmol) of triethylamine are dissolved in 50 ml of methylene chloride. At −10° C., a solution of 1.10 g (8.09 mmol) of isobutyl chloroformate in 20 ml of methylene chloride is instilled within 5 minutes and stirred for 20 minutes at −10° C. The solution is cooled off to −15° C., and a solution of 1.63 (8.09 mmol) of 11-aminoundecanoic acid and 2.43 mmol) of triethylamine in 50 ml of methylene chloride is instilled within 10 minutes and stirred for 30 minutes at −15° C., then overnight at room temperature. It is extracted twice with 100 ml each of 10% aqueous ammonium chloride solution, the organic phase is dried on magnesium sulfate and evaporated to dryness in a vacuum. The residue is chromatographed on silica gel (mobile solvent: methylene chloride/ethanol=20:1).

Yield: 4.41 g (68% of theory) of a colorless solid Elementary analysis: Cld: C 61.47 H 9.56 N 6.99 Fnd: C 61.53 H 9.48 N 6.89 b) 3,9 -Bis(carboxymethyl)-6-(10-carboxydecyl)-aminocarbonylmethyl-3,6,9 -triazaundecanedioic acid 4 g (4.99 mmol) of the title compound of Example 16a) is dissolved in 100 ml of trifluoroacetic acid. It is stirred overnight at room temperature. It is evaporated to dryness in a vacuum, and the residue is chromatographed on silica gel (mobile solvent: ethanol/25% ammonia water 20:1). The fractions containing the product are evaporated to dryness in a vacuum. The residue is dissolved in 100 ml of water. 16 ml of acid ion exchanger IR 120 ($H^+$ form) is added and stirred for 10 minutes at room temperature. It is filtered off from the ion exchanger and evaporated to dryness in a vacuum.

Yield: 1.95 g (63% of theory) of a vitreous solid Water content: 6.8% Elementary analysis (relative to anhydrous substance): Cld: C 52.07 H 7.69 N 9.72 Fnd: C 52.15 H 7.60 N 9.64 c) Gadolinium complex of 3,9-bis(carboxymethyl)-6-(10-carboxydecyl)-aminocarbonylmethyl-3,6,9-triazaundecanedioic acid-disodium salt 2.0 g (3.46 mmol) of the title compound of Example 16b) is suspended in 150 ml of deionized water and mixed at 80° C. in portions with 0.62 g (1.73 mmol) of gadolinium oxide. After a reaction time of 3 hours at 80° C., the now almost clear reaction solution is cooled off to room temperature, and pH 7.2 is set with 1N sodium hydroxide solution. After filtration, the obtained filtrate is freeze-dried.

Yield: 2.33 g (87.2% of theory) of an amorphous powder Water content: 8.13% Elementary analysis (relative to anhydrous substance): Cld: C 38.75 H 5.07 Gd 20.29 N 7.23 Na 5.93 Fnd: C 38.72 H 5.01 Gd 20.26 N 7.20 Na 5.89 d) Manganese complex of 3,9-bis(carboxymethyl)-6-(10-carboxydecyl)-aminocarbonylmethyl-3,6,9-triazaundecanedioic acid-trisodium salt 1.0 g (1.73 mmol) of the title compound of Example 16b) is suspended in 100 ml of deionized water and mixed at 80° C. in portions with 0.20 g (1.73 mmol) of manganese(II) carbonate. After a reaction time of 3 hours at 80° C., the now almost clear reaction solution is cooled off to room temperature, and pH 7.2 is set with 1N sodium hydroxide solution. After filtration, the obtained filtrate is freeze-dried.

Yield: 1.06 g (88.4% of theory) of an amorphous powder Water content: 8.83% Elementary analysis (relative to anhydrous substance): Cld: C 43.17 H 5.65 Mn 7.90 N 8.06 Na 9.92 Fnd: C 43.14 H 5.60 Mn 7.86 N 8.01 Na 9.88 e) Iron complex of 3,9-bis(carboxymethyl)-6-(10-carboxydecyl)-aminocarbonylmethyl-3,6,9-triazaundecanedioic acid-disodium salt 1.0 g (1.73 mmol) of the title compound of Example 16b) is suspended in 100 ml of deionized water and mixed at 80° C. in portions with 0.61 g (1.73 mmol) of iron(III) acetylacetonate. After a reaction time of 3 hours at 80° C., the now almost clear reaction solution is cooled off to room temperature, extracted twice with methylene chloride and a pH of 7.2 is set with 1N sodium hydroxide solution. After filtration, the obtained filtrate is freeze-dried.

Yield: 1.04 g (89.2% of theory) of an amorphous powder Water content: 8.11% Elementary analysis (relative to anhydrous substance): Cld: C 44.59 H 5.84 Fe 8.29 N 8.32 Na 6.83 Fnd: C 44.57 H 5.81 Fe 8.27 N 8.30 Na 6.80

What is claimed is:

1. A compound of formula I

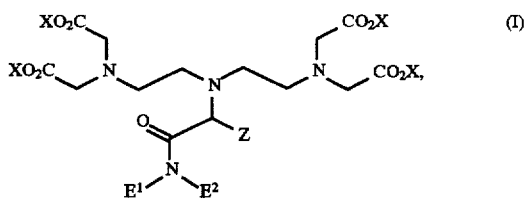

in which

X independently of one another, each stand for a hydrogen atom or a metal ion equivalent of an element of atomic numbers 20–29, 31, 32, 39, 42–44, 49 or 57–83, Z, $E^1$, and $E^2$ independently of one another, each stand for a saturated or unsaturated, branched or straight-chain $C_1$–$C_{50}$ alkyl chain wherein:
  the chain or parts of this chain optionally can form a cyclic $C_5$–$C_8$ unit or a bicyclic $C_{10}$–$C_{14}$ unit;
  the alkyl chain may also contain 0 to 10 oxygen and/or 0 to 2 sulfur atoms and/or 0 to 3 carbonyl, 0 to 1 thiocarbonyl, 0 to 2 imino, 0 to 2 phenylene, 0 to 1 3-indole, 0 to 1 methylimidazol-4-yl and/or 0 to 3 N—$R^3$ groups; and
  the alkyl chain is optionally substituted by 0 to 2 phenyl, 0 to 2 pyridyl, 0 to 5 $R^2O$, 0 to 1 HS, 0 to 4 $R^2OOC$, 0 to 4 $R^2OOC$—$C_{1-4}$ alkyl and/or 0 to 1 $R^2(H)N$ groups, in which optionally present aromatic groups can be substituted zero to five times, independently of one another, by fluorine, $R^2O_2C$, $R_2OOC$—$C_{1-4}$-alkyl, $C_{1-4}$-alkyl-NH, $R^2NHOC$, $R^2CONH$, $O_2N$, $R^2O$ and/or $R^2$ groups, $R^2$ independently of one another, each stand for a hydrogen atom or a straight-chain or branched $C_1$–$C_4$ alkyl radical and $R^3$ independently of one another, each stand for a hydrogen atom or a straight-chain or branched, saturated or unsaturated $C_1$–$C_{30}$ alkyl radical and $E^1$ and $E^2$ in addition to the above-indicated meaning, can each stand for a hydrogen atom or $E^1$ and $E^2$ together with inclusion of the nitrogen atom, can be a five- to eight-membered, saturated or unsaturated heterocycle, which optionally contains one to two additional nitrogen, oxygen or sulfur atoms and/or carbonyl groups, in which the HO and/or $H_2N$ and/or MS and/or HOOC group(s) optionally contained in Z, $E^1$ and/or $E^2$ can be present in protected form and in which free carboxylic acid groups not used for complexing can also be present as salts with physiologically compatible inorganic and/or organic cations or as esters or amides.

2. A compound according to claim 1, which is a complex having a central atom which is an element of atomic numbers 21–29, 42, 44 or 57–83.

3. A compound according to claim 1, wherein all radicals X stand for a hydrogen atom.

4. A compound according to claim 1, which is a complex having a central atom which is a radioisotope of an element of atomic numbers 21, 26, 27, 29, 31, 32, 39, 43, 49, 62–64, 66, 70, 75, 77 or 83.

5. A compound according to claim 1, wherein at least one of radicals $E^1$ and $E^2$ stands for hydrogen or a methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, or n-icosyl radical, or wherein $E^1$ and $E^2$ together with the connecting nitrogen atom stand for a morpholine radical.

6. A compound according to claim 1, wherein at least one of radicals $E^1$ and $E^2$ stands for a 2-hydroxyethyl chain or for a radical of formula II

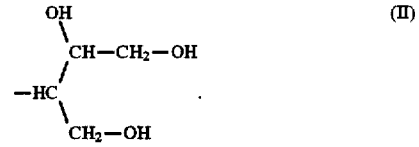

7. A compound according to claim 1, wherein at least one of radicals $E^1$ and $E^2$ stands for a radical

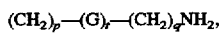

in which
  G stands for oxygen or sulfur,
  p and q independently of one another, each stand for a number of from 1 to 28,
  t stands for 0 or 1, and p+t+q≦30, where the amino group can also be present as an ammonium salt with a physiologically compatible anion of an inorganic or organic acid.

8. A compound according to claim 1, wherein Z stands for the methyl, ethyl, propyl, i-propyl, butyl, i-butyl, tert-butyl, pentyl, hexyl, or cyclohexyl radical.

9. A compound according to claim 1, wherein Z stands for a phenyl or benzyl radical, which optionally is substituted zero to five times, independently of one another, by fluorine $R^2O_2C$, $R^2OOC$—$C_{1-4}$alkyl $C_{1-4}$-alkyl-NH, $R^2NHOC$, $R^2CONH$, $O_2N$, $R^2O$, and/or $R^2$ groups, in which $R^2$ stands for a hydrogen atom or a branched or unbranched $C_1$–$C_4$ alkyl radical.

10. A compound according to claim 1, wherein Z is identical with radical $Z^A$ of a naturally occurring α-amino acid of general formula III

11. A compound according to claim 10, wherein the amino acid is alanine, valine, leucine, phenylalanine, tyrosine, serine, threonine, cysteine, methionine, tryptophane, aspartic acid, glutamic acid, arginine, lysine or histidine.

12. Pharmaceutical agents containing at least one physiologically compatible compound according to claim 1, optionally with the additives usual in galenicals.

13. A compound of formula I

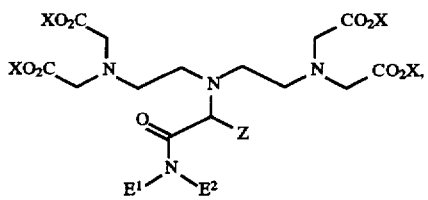

in which
- X independently of one another, each stand for a hydrogen atom or a metal ion equivalent of an element of atomic numbers 20–29, 31, 32, 39, 42–44, 49 or 57–83,
- Z, $E^1$, and $E^2$ independently of one another, each stand for a saturated or unsaturated, branched or straight-chain $C_1$–$C_{50}$ alkyl chain wherein:
  - the chain or parts of this chain optionally can form a cyclic $C_5$–$C_8$ unit or a bicyclic $C_{10}$–$C_{14}$ unit;
  - the alkyl chain may also contain 0 to 10 oxygen and/or 0 to 2 sulfur atoms and/or 0 to 3 carbonyl, 0 to 1 thiocarbonyl, 0 to 2 imino, 0 to 2 phenylene, 0 to 1 3-indole, 0 to 1 methylimidazol-4-yl and/or 0 to 3 N-$R^3$ groups; and
  - the alkyl chain is optionally substituted by 0 to 2 phenyl, 0 to 2 pyridyl, 0 to 5 $R^2O$, to 1 HS, 0 to 4 $R^2OOC$, 0 to 4 $R^2OOC$-$C_{1-4}$ alkyl and/or 0 to 1 $R^2(H)N$ groups, in which optionally present aromatic groups can be substituted zero to five times, independently of one another, by fluorine, $R^2O_2C$, $R^2OOC$—$C_{1-4}$-alkyl, $C_{1-4}$-alkyl-NH, $R^2NHOC$, $R^2CONH$, $O_2N$, $R_2O$ and/or $R^2$ groups,
- $R^2$ independently of one another, each stand for a hydrogen atom or a straight-chain or branched $C_1$–$C_4$ alkyl radical and
- $R^3$ independently of one another, each stand for a hydrogen atom or a straight-chain or branched, saturated or unsaturated $C_1$–$C_{30}$ alkyl radical and $E^1$ and $E^2$ in addition to the above-indicated meaning, can each stand for a hydrogen atom, provided that at least one of radicals $E^1$ and $E^2$ stands for a radical —$(CH_2)_p$—$(G)_t$—$(CH_2)_q$COOH, in which G stands for oxygen or sulfur, p and q independently of one another, each stand for a number of from 1 to 28, t stands for 0 or 1, and p+t+q$\leq$30, where the acid group can also be present as a salt of an inorganic or organic base, as an ester, or as an amide, in which the HO and/or $H_2N$ and/or HS and/or HOOC group(s) optionally contained in Z, $E^1$ and/or $E^2$ can be present in protected form and in which free carboxylic acid groups not used for complexing can also be present as salts with physiologically compatible inorganic and/or organic cations or as esters or amides.

14. A method for NMR diagnosis or diagnostic radiology which comprises administering to patient a physiologically compatible compound according to claim 1.

15. A method for diagnostic radiology or radiotherapy which comprises administering to patient a physiologically compatible compound according to claim 1.

* * * * *